United States Patent
Philbert et al.

(10) Patent No.: US 7,923,984 B2
(45) Date of Patent: Apr. 12, 2011

(54) UNIVERSAL, WIRELESS, NANO-OPTICAL VOLTMETERS

(75) Inventors: Martin A. Philbert, Northville, MI (US); Katherine M. Tyner, Silver Spring, MD (US); Raoul Kopelman, Ann Arbor, MI (US)

(73) Assignee: The Regents of the University Of Michigan, Ann Arbor, MI (US)

( * ) Notice: Subject to any disclaimer, the term of this patent is extended or adjusted under 35 U.S.C. 154(b) by 457 days.

(21) Appl. No.: 12/015,674

(22) Filed: Jan. 17, 2008

(65) Prior Publication Data
US 2008/0297137 A1 Dec. 4, 2008

Related U.S. Application Data

(60) Provisional application No. 60/881,485, filed on Jan. 19, 2007.

(51) Int. Cl.
*G01R 19/02* (2006.01)
(52) U.S. Cl. .......................................... 324/96; 977/788
(58) Field of Classification Search .................... 324/96; 977/700, 773, 788
See application file for complete search history.

(56) References Cited

OTHER PUBLICATIONS

C.-B. Chien & J. Pine., Voltage-Sensitive Dye Recording of Action Potentials and Synaptic Potentials from Sympathetic Microcultures, 60 Biophys. J. 697-711 (1991).*
C. Graf et al., Dye-Labeled Poly(Organsiloxane) Microgels with Core-Shell Architecture, 15 Langmuir 6170-6180 (1999).*
P. J. Campagnola et al., High-Resolution Nonlinear Optical Imaging of Live Cells by Second Harmonic Generation, 77 Biophys. J. 3341-3349 (1999).*
R. Haag, Supramolecular Drug-Delivery Systems Based on Polymeric Core-Shell Architectures, 43 Angew. Chem. Int. Ed. 278-282 (2004).*
K.-Y. Pu et al., Fluorescent Single-Molecular Core-Shell Nanospheres of Hyperbranched Conjugated Polyelectrolyte for Live-Cell Imaging, 21 Chem. Mater. 3816-3822 (2009).*

* cited by examiner

*Primary Examiner* — Glenn Caldarola
*Assistant Examiner* — Randy Boyer
(74) *Attorney, Agent, or Firm* — Harness, Dickey & Pierce, P.L.C.

(57) ABSTRACT

A universal, wireless, nano-optical voltmeter comprises an organic core having at least one voltage-sensitive dye and at least one polymeric shell substantially surrounding the organic core. The nano-optical voltmeter can detect electric fields in cells. The nano-optical voltmeter allows three-dimensional E field profiling throughout the entire volume of living cells. The nano-optical voltmeter may be calibrated externally and then applied for E field determinations inside any live cell or cellular compartment, with no further calibration steps.

10 Claims, 25 Drawing Sheets

UNIVERSAL, WIRELESS, NANO-OPTICAL VOLTMETERS

CROSS-REFERENCE TO RELATED APPLICATIONS

This application claims the benefit of U.S. Provisional Application No. 60/881,485, filed on Jan. 19, 2007. The disclosure of the above application is incorporated herein by reference.

GOVERNMENT RIGHTS

This invention was made with government support under Grant No. F49620-03-1-0297 awarded by the Air Force Office of Scientific Research and Grant No. DMR0455330 awarded by the National Science Foundation. The government has certain rights in the invention.

FIELD

The present disclosure relates to universal wireless nano-optical voltmeters and methods of using nano-optical voltmeters for measuring electric fields.

Introduction

Electric fields (E fields) are found in and surrounding every living cell and are critical for the proper functioning of biological processes. These electric fields are as widely varied as the high internal fields that preserve the cells' energy-dependent non-equilibrium chemical steady state, or the cell-to-cell signaling fields in complex organisms. Biological electric fields can affect the entire human body, such as the E fields associated with neural signals or the cardiac rhythm. Major E fields are also found in volumetrically small components of cells, such as the mitochondria. The E fields associated with the mitochondrial membrane are relatively large, with a highly polarized inner membrane potential, as high as −150 mV. Dividing the membrane potential by the distance that the potential spans (the width of the membrane, ~5 nm), produces an E field on the order of $-3 \times 10^7$ V/m. Changes in E fields can indicate perturbations in biological function, such as observed in Alzheimer's disease (reduction of the E field associated with the neuronal membrane potential) or cell death (loss of the E field associated with the mitochondrial membrane).

Externally applied E fields have been employed in the modulation of a variety of physiological and pathophysiological processes and significant alteration/adaptation of cellular regulatory processes have been achieved. In the clinical management of wound healing, external E fields have been shown to accelerate repair. Both endogenous and applied E fields have been demonstrated to stimulate Xenopus nerve growth and regeneration. Exposure of cells in culture to short E field pulses induces electroporation of membranes for the delivery of nucleotides, peptides and small proteins; many of these are under development as therapeutics. External E fields have also been shown to induce mitochondria to fuse and to stimulate gene expression. However, with available technologies it remains difficult to assess the effect of external fields on many intracellular components, in the live cell.

With both external and internal cellular E fields producing wide-ranging biological effects, the ability to measure complete electric profiles (charge-coupled gradients and fields) of cells would greatly enhance the understanding of biological processes. The measurement of electric fields in biology and, in particular, cellular biology has been limited to membrane-dependent methods, be they voltage sensitive dyes, patch and voltage clamps, Green Fluorescence Protein (GFP) methods, or Fluorescence Resonance Energy Transfer (FRET) techniques, i.e., limited to less than 0.1% volume fraction of the cell.

Despite being generated by the segregation and passage of ions in and through biological membranes, the resulting E fields have profound effects on a variety of nonmembranous functions. However, the distances that such E-fields extend beyond an associated membrane, and the range of their influence, remain largely unmeasured and unknown. As a result, there are wide gaps in the descriptions of cellular E field profiles, and characterization thereof would greatly enhance current knowledge of cellular organization and signaling. For example, there is a proposed three-dimensional E field signaling network that has the nucleus at the center and extends throughout the entire cell, with the endoplasmic reticulum (ER) or actin wires and microtubules forming the network. Such a system cannot be detected or readily quantified with currently available techniques. In addition to limiting E field characterizations to membranes, the current methods used to measure E fields are often invasive (patch and voltage clamps, microelectrodes), or their measurements exhibit cell-to-cell variation (voltage dyes), resulting in lengthy voltage calibrations or significant inaccuracies.

Voltage sensitive dyes provide a one optical method for the measurement of many electrical phenomena within cellular environments. For instance, these dyes are typically used to follow changes in electric fields that arise from cellular membrane potentials. Slow response dyes comprised of cationic lipophilic molecules such as 5,5',6,6'-tetrachloro-1,1',3,3'-tetraethylbenzimidazolylcarbocyanine iodide (JC-1 cationic carbocyanine dye), rhodamine 123, tetramethylrodamine methyl ester or tetramethylrhodamine ethyl ester have been used to probe the loss of mitochondrial membrane potentials associated with the mitochondrial permeability transition pore (MPTp) through translocation in response to changes in the electric field. Alternatively, fast response, zwitterionic dyes are embedded into cellular membranes, and have been used to measure fast electrical changes in cells, such as action potentials, optical signals, and cortical dynamics. Other technologies such as patch and voltage clamps, Green Fluorescent Protein (GFP) methods, and Fluorescence Resonance Energy Transfer (FRET) techniques also involve direct interactions with, or are constrained to specific components of the cellular membrane.

However, neither the slow-response class nor the fast response class of dye is optimal for determining electric fields throughout an entire cell. In addition, the dyes respond differently in various membrane environments. As a result, these dyes need to be calibrated to individual cells and individual membranes through methods such as patch and voltage clamps (a bulky, membrane-based method, that is often too large to probe local electrical changes), or a valinomycin method (artificial ion gradients are imposed upon the cells). In addition, some dyes have been found to be cytotoxic. There is a need for better ways of ascertaining E fields generated by the segregation and passage of ions in and through biological membranes and/or E fields generated non-membranous functions.

SUMMARY

Embodiments of the present technology include compositions and methods for the design, synthesis, and biological application and use of a universal, autonomous, wireless, nano-sized, "photonic voltmeter"—a nano-optical voltmeter (NOV). The NOV is not confined to the exploitation of the properties of lipid bilayers during changes in E fields. These NOVs allow for three-dimensional intracellular identification and quantification of electric fields. Electric fields of interest may result not only from membrane potentials, but also from any electric potential that may arise intracellularly.

In some embodiments, the NOV is a particle composed of an organic core surrounded by at least one polymeric shell for general inhibition of particle aggregation. The polymeric shell may be comprised of polymerized silane reacted with a silane capping group. The shell may be further modified by the attachment of organic and/or inorganic targeting molecules, or coated with materials to allow for enhanced performance. Any suitable voltage sensitive dye may be encapsulated by the organic core of the particle. The optical properties of the dye are used to correlate an optical response to changes in any electric field (E field). In some embodiments, NOVs include "Electro-Photonic Explorer for Biomedical use with Biologically Localized Embedding," or E-PEBBLEs.

Embodiments of E-PEBBLEs include Photonic Explorer for Biomedical use with Biologically Localized Embedding (PEBBLE) technology used to measure analytes such as calcium, potassium, nitric oxide, oxygen, etc. inside cultured cells, as well as physical properties including viscosity. In some embodiments, E-PEBBLEs allow for the use of multiple sensor systems in a living cell to simultaneously determine not only the chemical, but resulting physical properties of biological processes.

In some embodiments, the E-PEBBLEs comprise nanoparticles that encapsulate the fast response, voltage sensitive dye di-4-ANEPPS. The dye's fluorescence spectrum shifts in response to changing E fields. This shift can be analyzed ratiometrically, greatly reducing any background noise in the sample. The dye is encased in the hydrophobic core of a silane capped mixed micelle, which provides a uniform environment for the dye molecules. These nanoparticles are universally applicable in the sense that they are calibrated prior to use and are inserted as calibrated nanoprobes into any cell, cellular compartment, or external region (including non-cellular systems), without the requirement for further calibration. These nanoprobes also allow for the measurement of E fields in the cytosol and the ability to construct complete cellular E field profiles through the use of confocal microscopy. In addition, the E-PEBBLEs can be used as nanoprobes to ascertain the role of cellular E fields in influencing and/or regulating biological processes, with wider implications for cellular biology, biophysics, and biochemistry.

Further areas of applicability of the present teachings will become apparent from the detailed description provided hereinafter. It should be understood that the detailed description and specific examples, while indicating various embodiments of the teachings, are intended for purposes of illustration only and are not intended to limit the scope of the teachings.

BRIEF DESCRIPTION OF THE DRAWINGS

The present teachings will become more fully understood from the detailed description and the accompanying drawings, wherein.

DESCRIPTION

Figure 1:
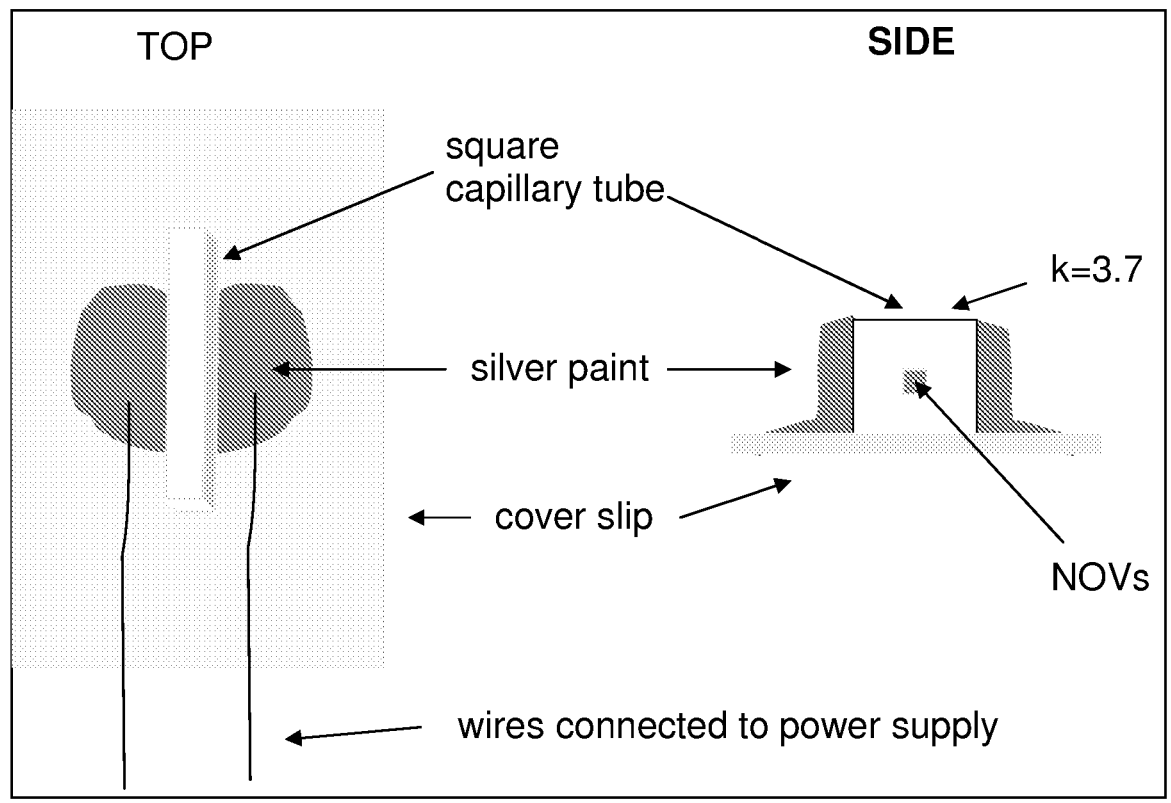
FIG. 1 schematically shows an external calibration device for nano-optical voltmeter particles.

The following description of technology is merely exemplary in nature of the subject matter, manufacture, and use of one or more inventions, and is not intended to limit the scope, application, or uses of any specific invention claimed in this application or in such other applications as may be filed claiming priority to this application, or patents issuing therefrom.

The present description details the synthesis, characterization, and utilization of novel, universal, wireless, optical nano-voltmeters (NOV), such as E-PEBBLEs. These nanoparticles can be used as nanoprobes to detect rapid fluctuations of electric fields (E fields) in cells, including the non-membrane regions such as the cytosol. These E field sensing nanoparticles allow for three dimensional imaging of these various E fields.

A schematic of one embodiment of an E-PEBBLE constructed in accordance with the present teachings is shown in FIG. 10A. E-PEBBLEs include one or more voltage sensitive dyes. The E-PEBBLE may comprise mixed micelles coated with organo-silanes or silane coated microemulsions that are embedded with a fast response voltage dye, for example, pyridinium, 4-(2-(6-(dibutylamino)-2-naphthalenyl)ethenyl)-1-(3-sulfopropyl)-, hydroxide, inner salt (Di-4-ANEPPS). Di-4-ANEPPS has a ratiometric response to changes in the surrounding electric field measurable by fluorescence emission intensity. Measurement of the ratiometric response helps eliminate drift or noise resulting from photobleaching and/or optical instability. A fast response voltage-sensitive dye embedded in individual nano-optical voltmeters may also be optically measured by other means, for example, using luminescence or by analysis of an absorbance spectrum.

As the dye is encapsulated in the E-PEBBLE nanoparticles, the particles may be calibrated using an external device and then applied to any medium, including a cell or cellular moiety. Thus, E-PEBBLEs are universal in regards to the facile exterior calibration and range of measurable moieties.

Mixed micelles coated with organo-silanes or silane coated microemulsions may be further capped with a silane to inhibit aggregation. Inhibition of particle aggregation may be necessary to allow the E-PEBBLE particles to enter the cells. In addition, the particles may be subsequently coated with a material to change the particle from having a slightly negative charge to a slightly positive charge. This can help in preventing cytotoxic effects and/or cell death. The E-PEBBLE particle shell may also be modified by the attachment of organic and/or inorganic targeting molecules, or coated with materials to allow for enhanced performance. Targeting may include, but is not limited to, targeting by charge, charge distribution, pH, magnetic properties, "stickiness", and evasion of immune cells. The nano-optical voltmeter particles may be about 1 nm to about 100 nm in diameter. Diameter of the nano-optical voltmeter particles can be adjusted by changes in the micelles and emulsions used to form the particles. In some cases, the population of nano-optical voltmeter particles may have substantially the same diameter.

The E-PEBBLEs may be dispersed into the cytosol and/or the nucleus for measurement of E fields, for example, and may be used to examine changes in the mitochondrial membrane potential and in the potentials of the surrounding cytosol.

The E-PEBBLEs may also be used to determine E fields in environments of non-biological or biological origin. The E-PEBBLEs may be employed in isolation or as a composite part of a larger system that is used to detect and/or measure E fields in all environments that transmit light such as, but not limited to fluids, emulsions, multiphase solutions, suspensions, organic/inorganic solutions, complex mixtures, gels, gases, vapors, aerosols, metal/non metal surfaces, coatings, films, composites, devices/materials with complex planar and non-planar geometries, macro-/micro-/nano-electronic and non-electronic devices, microbiological films and suspensions, plant and/or animal organisms, organs, tissues, cells, subcellular compartments, isolated and/or cultured organs, cells, and tissue slices.

The E-PEBBLEs may also be used to calibrate electric devices or for the purpose of imaging. The E-PEBBLEs have application in medical devices, including incorporation into "smart drug delivery devices" whereby the sensing of a particular electric field either directs the targeting of the therapeutic or causes the release of a payload. The E-PEBBLEs may be incorporated into nano-sized homing devices, or through incorporation into thin films, used for flat panel sensors.

Referring again to FIG. 10A, the E-PEBBLE may include the fast response, voltage-sensitive dye di-4-ANEPPS embedded in the organic core of a mixed micelle formed from a long-chain organosilane and surfactant. The silane headgroups are polymerized to form a thin silane shell around the micelle, which stabilizes the particle. A second silane layer containing a primary amine may be added at this point to allow for the bioconjugation of targeting molecules (targeting layers and targeting molecules are not included in the reported particle and are not discussed in this article). A final silane capping layer composed of a monoethoxy silane may then be added to react with any excess silane headgroups. This capping layer can prevent aggregation of the particles. Surfactant and excess silane may be removed from the particle solution with dialysis. In some cases, an additional exterior coating of poly(diallyldimethylammonium chloride) is applied to the nanoparticles to allow for cellular uptake.

The dye is depicted in FIG. 10A to be localized inside the oily core of the nanoparticle. As the dye is hydrophobic, it will preferentially localize into the organic regions of the nanoparticle solution. The dye experiences a blue shift in the emission peak as it goes from a free dye dissolved in chloroform to being encapsulated inside the nanoparticle. This blue shift is similar to the emission shift that occurs when the free dye is bound to a membrane. The dye molecules are shown oriented in an E field due to the fact that there is not an observed isotropic cancelling of the dye's fluorescent emission response when the E field changes. The actual orientation of the dye molecules is unknown, and the schematic represents only one possible arrangement of the dye molecules.

Using a fast response, voltage-sensitive dye that is internally ratiometric (i.e., no reference dye is needed to form the ratio) provides several advantages, even when not encapsulated in a nanoparticle matrix. Such advantages include reduction in motion artifacts, noise cancellation of laser and experimental fluctuations, normalization for differences in local sensitivity, photobleaching correction, and enhanced voltage sensitivity. When the dye is encapsulated in a uniform nanoparticle matrix, the dye's response is further enhanced as fluctuations that occur in the cell and would affect the free dye (membrane rearrangement, fluidity changes, etc.) are eliminated. The uniform environment allows the particles to be calibrated externally and applied to cells or cellular compartments with no further calibration steps.

The E-PEBBLEs have several advantages over other methods used to determine E fields associated with organelles in intact cells. Although TMRM and other voltage-dependent free dyes are used widely to both visualize and characterize E field changes of mitochondrial membranes, these dyes are often in the class of "slow response dyes". The positively charged molecules of a slow response dye physically translocate across the mitochondrial membrane, in response to changing E fields. With higher E fields, more dye molecules move across the membrane toward the more negative regions of the cell (mitochondria). When the CCCP decreases the E field associated with the mitochondrial membrane, the molecules can "leak" out of the mitochondria, as the strong negative region has dissipated. Since this mechanism involves molecules physically moving across membranes, it can be a slow process. Indeed, depending on concentration and local conditions, the dye may take several minutes to respond to significant E field changes. Di-4-ANEPPS, however, is a fast response voltage dye. The fast response class of molecules embeds within the lipid bilayer itself and changes its fluorescence spectra due to changes in the local environment (electrochromatic changes, orientation, aggregation, etc.). Di-4-ANEPPS exhibits electrochromatic changes in response to changing E fields. Due to the fact that the fast response dyes undergo only small changes, these dyes respond within milliseconds to changing E fields. The fast response property of the dye, even when embedded within the particles, allows for the identification and isolation of rapid fluctuations in the mitochondrial membrane potential and can provide a substantial improvement in the ability to measure temporal changes in a variety of other cellular and nonbiological systems. Note that with both classes of free dyes, the traditional molecules, and hence the E field measurements, are confined to the membranes, either by direct embedding or by translocating across the lipid bilayers. Thus, E fields extending into nonmembrane regions of the cells or membranes that are difficult to stain with voltage dyes cannot be measured. In contrast, as the E-PEBBLEs are self contained units, they can report any E fields throughout the entire cell. Although the dye molecules are possibly no longer oriented the way they are in a biological membrane, the nanoparticles still show an optical response to changing E fields, possibly due to the fact that the organic core of the particle allows for some type of orientation of the molecules in an E field.

The present universal, wireless, nanosized, autonomous, "photonic voltmeter" may be used to provide complete E field imaging of a live cell. The voltage-sensitive nanoparticles can detect fluctuations of E fields throughout the entire cell, including nonmembrane regions. The use of these particles opens up the potential for the determination, with three-dimensional spatial and temporal resolution, of biological sequelae resulting from modulation of hitherto immeasurable E fields that extend into the cytosol and other regions of the cell. These new nanosensors greatly enhance the potential for integrating real-time measurements of intracellular/extracellular E-fields with investigations of voltage-dependent cellular processes that are not immediately proximal to polarized membranes. Such imaging of an entire cell's E fields can also be integrated with chemical and physical imaging of the live cell, resulting in real high-dimensional images of cells, including multiple physical (space, fields, temperature, viscosity) and chemical (ions, molecules, radicals) dimensions. Furthermore, these first "nanosize voltmeters" also open the way for wireless E-field profiling, with minimal "cross talk," inside micro/nanoelectronic devices.

The following examples illustrate embodiments of compositions, methods of producing compositions, and methods of using compositions of the present technology.

EXAMPLE 1

Synthesis of a Nano-Optical Volmeter (NOV)

Octyldecyltriethoxysilane was purchased from Pfaltz and Bauer (Waterbury, Conn.). Square glass capillary tubes were obtained from Polymicro Technologies, LLC (Phoenix, Ariz.). Silver paint was purchased from SPI Supplies (West Chester, Pa.). Di-4-ANEPPS was purchased from Molecular Probes (Eugene, Oreg.). All other chemicals were purchased from Sigma-Aldrich (St. Louis, Mo.) and used as received. All water noted in the methods is deionized water.

Silane capped mixed micelles were formed as follows. Triton X-100 (0.625 g, 1 mmol) was dissolved in 10 mL of deionized water. Octyltriethoxysilane (63 µL, 0.2 mmol) was slowly added and the solution allowed to stir for 30 minutes. Ammonium hydroxide (10-20 µL of a 2.2 M solution) was added, and the solutions were stirred for 72 hours. Trimethylethoxysilane (200 µL, 1.3 mmol) was added, and the solutions allowed to stir for an additional 48 hours.

Silane capped microemulsions were formed as follows. Brij 97 (1.5 g, 2.12 mmol) and DOS (45 µL, 0.096 mmol) were stirred in water (8 mL, 444.0 mmol) at 65° C. for 15 minutes. The solution became milky white (2-3 min) and then cleared (after approximately 5-10 min). The solution was allowed to cool while stirring. Octadecyltriethoxysilane (76.7 µL, 0.16 mmol) was added to the mixed solution and the solution was again stirred for 15 minutes at 65° C. The solution was allowed to cool to room temperature. Sulfuric acid (1 µL of a 2 M solution, 0.002 mmol) was added to the mixture and allowed to stir for 30 minutes. Water was added to the mixture (2 mL, 111.0 mmol), along with sodium hydroxide (38.5 µL of a 2 M solution, 0.077 mmol) and tetraethoxyorthosilicate (73.3 µL, 0.329 mmol), and the solution was stirred for 1 hour. Trimethylethoxysilane (450 µL, 2.88 mmol)) was added and the solution stirred for 72 hours.

Cleaning, coating, and loading of the NOV were performed as follows. The solutions were dialysized for 24 hours in a Spectra/Por polyvinylidene difluoride (PVDF) dialysis membrane from Spectrum Labs with a 250 kDa molecular weight cut-off (MWCO). The water bath was changed three times during the dialysis. The solution was then stirred with an equal volume of a 1 wt % solution of poly(diallyldimethylammonium chloride) (low molecular weight) and again dialyzed for 24 hours with three changes of the water bath. A 1 mL aliquot of the washed and coated particles was sonicated with a 10 µL solution of di-4-ANEPPS dissolved in chloroform (0.1 mg/mL, 0.2 mM). The solution turned cloudy, and then a stirbar was added and the solution was stirred under an aluminum foil tent for 30 minutes to remove the chloroform. Solutions were stored in the dark at room temperature.

Figure 2:
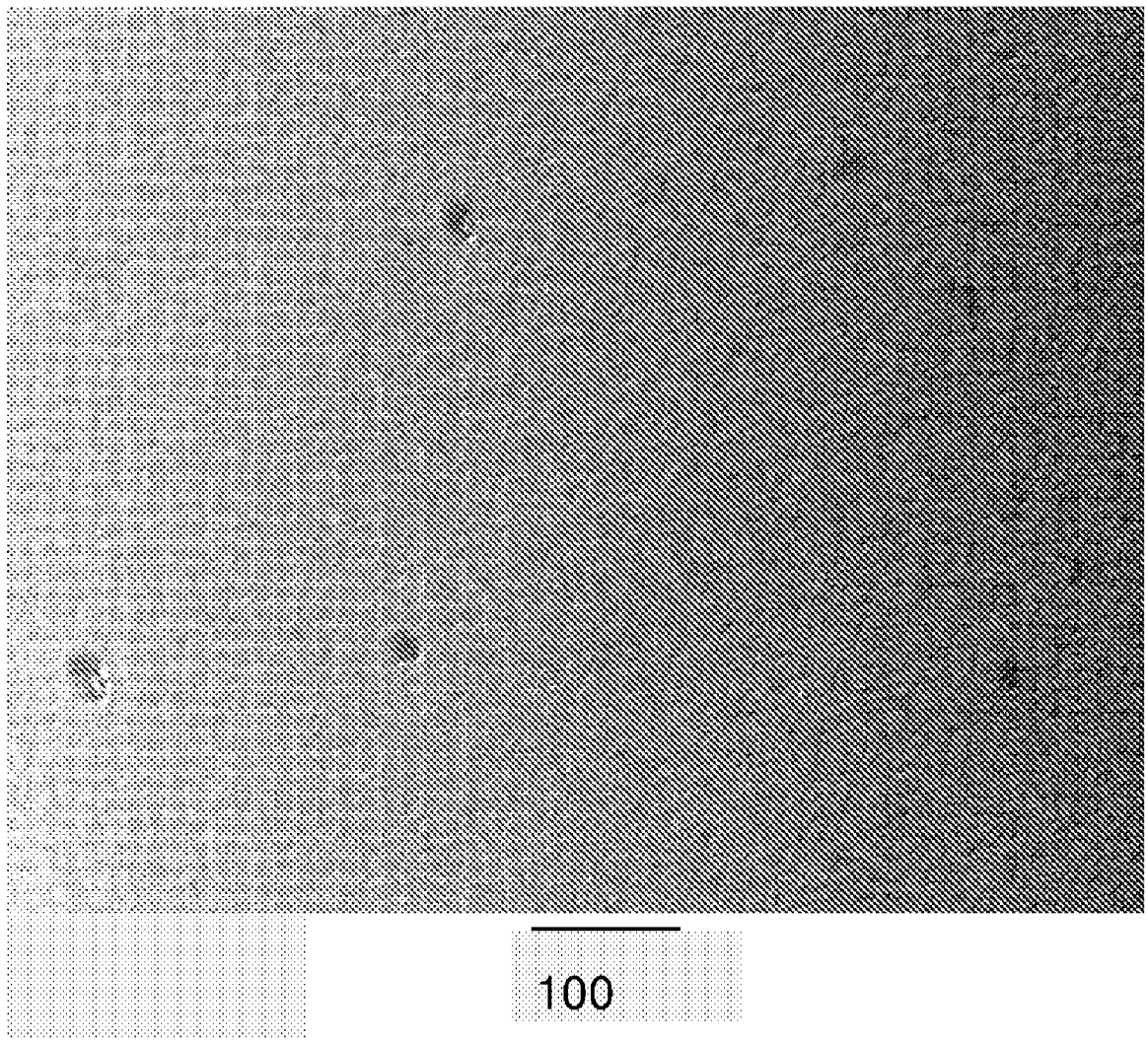
FIG. 2 shows size characterization of nano-optical voltmeter particles by transmission electron microscopy, with the scale bar equal to 100 nm.
Figure 3:
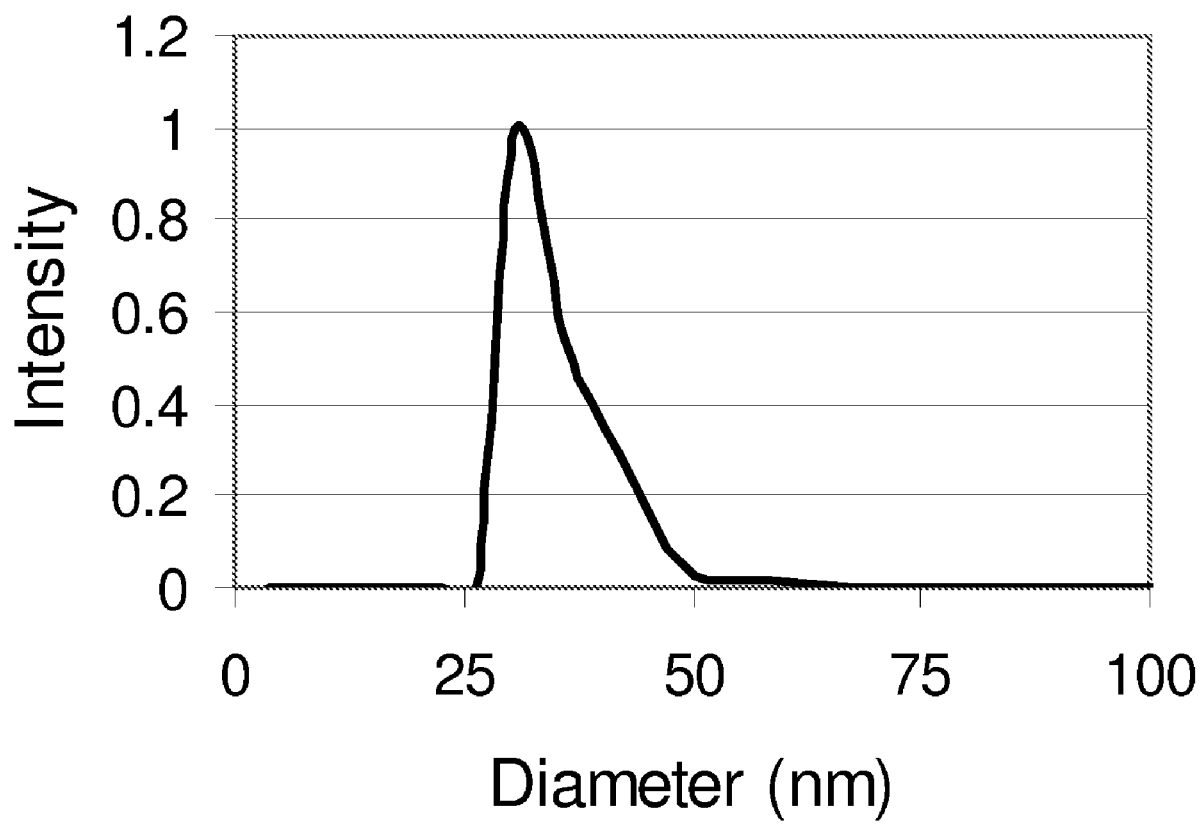
FIG. 3 is a graph illustrating size characterization of nano-optical voltmeter particles by light scattering analysis.

Particles were analyzed with transmission electron microscopy (TEM) to determine morphology and size of the particles. To verify the TEM images, light scattering was also performed on the particles. FIGS. 2 and 3 show the size characterization of the particles. The particles while not strictly mono-disperse, are tightly distributed around the mean hydrodynamic diameter of 30 nm with minimal variation from the mean. The approximate zeta potential of the particles was approximately 14 mV. Early iterations of the NOV demonstrate clearly that the membrane/fluid-like interior of the nanoparticle is critical for proper functioning. Therefore, other particles with oily/fluid-like interiors could also be used as nano-sized voltmeters. Moreover, the particles can incorporate more than one dye, enabling the addition of either a reference dye, or a variety of fast-response dyes, to the original voltage dye thereby augmenting the range of response of a single nanoparticle. In some cases, the reference dye is not voltage-sensitive.

EXAMPLE 2

Characterization and Method of Calibration of the NOV

The NOV synthesized in Example 1 was characterized as follows. Cleaned emulsions were analyzed through transmission electron microscopy. Samples were prepared by dropping 15 μL of the particle suspension onto a 400 mesh carbon coated copper grid and letting the grid dry overnight. Samples were analyzed on a JEOL 3011 High Resolution Electron Microscope. Particle solutions were also analyzed with a PSS Nicomp 300 ZLS particle analyzer in the Kyung-Dall Lee laboratory in the College of Pharmacy, University of Michigan, using the number weighted distribution.

Voltage calibration and calibration device fabrication were performed as follows. Cleaved portions of square capillary tubes (inner diameter of 52 microns and a glass outer diameter of 300 microns) were stripped of their polyimide coating by soaking in concentrated sulfuric acid at 150° C. for 5 minutes. The stripped tubes were then soaked in deionized water for 30 minutes and finally soaked in 95% ethanol for 30 minutes. The tubes were allowed to dry overnight. The stripped tubes were cleaved into small pieces and loaded with NOV solution. The tubes were affixed to glass cover slips with a clear varnish (Revlon clear 771). The varnish was allowed to dry for 30 minutes before the sides of the device were painted with silver paint and allowed to dry overnight. FIG. 1 shows a schematic of the external calibration device.

External calibration of the NOV was performed as follows. The calibration device was taped to the stage of a confocal microscope (Olympus IX70 connected to a Life Science Resources UltraView equipped with an Ar—Kr laser and a Lambda 10-2 sutter wheel from Sutter Instrument Co.). Wires were connected to the device through application of silver paint, and the electric field modulated with a Bio-Rad PowerPac1000. The voltage was allowed to stabilize for 1 minute before taking a measurement. The power supply was then allowed to rest at 0 Volts for 1 minute before a new voltage was entered. The NOVs were excited at 488 nm. Emission images were collected at 600 nm (50 nm band pass) and 700 nm (50 nm band pass) with Perkin Elmer UltraView imaging software in Temporal mode.

Image Analysis was performed as follows. The images were transferred to the image analysis package MetaMorph from Molecular Devices, and a rectangular region of interest was chosen spanning the length of the capillary channel. The average pixel intensity ratio of the 600 nm image versus the 700 nm image was calculated and plotted versus electric field. In some cases the change in ratio (from zero, $\Delta R/R$) was plotted versus electric field. The electric field was calculated by taking the E field at 300 microns and dividing by dielectric constant of the silica (3.7) as reported in the product literature. At least four to six trials were completed and used to provide the arithmetic mean and standard deviation prior to performance of a regression analysis to determine the slope, intercept, and errors of the calibration curve. The values for slope and intercept were used when analyzing cellular systems using the background fluorescence outside the cell volume as the reference intensity (E=0 V/m).

Figure 4:
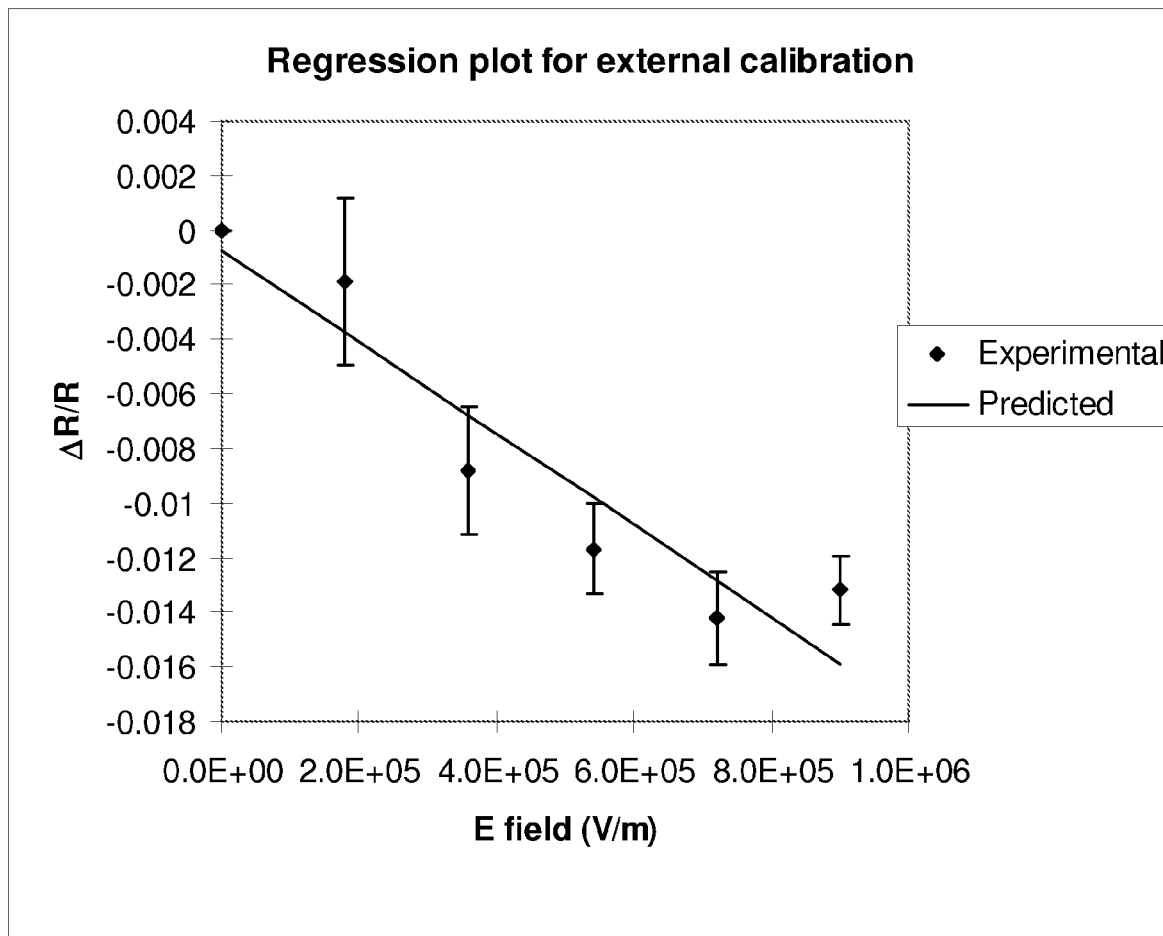
FIG. 4 is a graph illustrating a representative external calibration curve for the mixed-micelle silane nanoparticles.

FIG. 4 contains a representative external calibration curve for the mixed-micelle silane nanoparticles. The NOV solution or dried gel is loaded into capillary tubes that then have their sides coated with silver paint. The electric field may be modulated through use of a power supply connected to the silver paint through the use of wires. As the electric field experienced by the nanoparticles increases, the emission ratio of the embedded dye decreases. The raw curves are then transformed into "change in emission ratio over emission ratio" ($\Delta R/R$), by subtracting the emission ratio at a certain E field by the emission ratio when there is no E field present. This function allows the individual calibration curves to be averaged together and have an error analysis performed upon them. The slope and y intercept for the batch of NOV was $-8.5 \times 10^{-9}$ ($-9 \times 10^{-9} +/-2$) and 0.002 (0.002+/-1), respectively. These values from the external calibration are then used in determining the E field in cells, without having to individually calibrate the cells.

EXAMPLE 3

Methods of Using the NOV to Measure Cellular E-Fields

Cell Experiments and Cellular Materials were performed as follows. The NOVs synthesized in Example 1 were used in these experiments. C6 glioma cells and DITNC astrocytes were obtained from the American Type Culture Collection. Hanks balanced salt solution (HBSS), Dulbecco's modified eagle medium (DMEM), fetal bovine serum (FBS), and penicillin-streptomycin (p/s) were obtained from Invitrogen. Tetramethylrhodamine, methyl ester (TMRM) was purchased from Molecular Probes. All other chemicals were purchased from Sigma-Aldrich. Carbonyl cyanide 3-chlorophenylhydrazone (CCCP) and TMRM were first dissolved in dimethyl sulfoxide to make stock solutions.

Depolarization, comparison with TMRM, and cytosol measurements were performed as follows. Mouse C6 glioma cells were plated on to glass cover slips at a concentration of approximately $2.5 \times 10^5$ cells/mL. Cells were incubated in DMEM supplemented with 10% FBS and 1% p/s overnight. The media was then removed and replaced with fresh media. NOVs were added to the suspension (125-250 μg particles) and the cells incubated for 30 minutes. The cover slip was rinsed with HBSS containing 10 mmol N-2-Hydroxyethylpiperazine-N'-2-Ethane Sulfonic Acid (HEPES) and placed in a stainless steel cell chamber with 1 mL HBSS containing 10 mmol HEPES. In some cases TMRM dissolved in dimethyl sulfoxide was added to the chamber for a total concentration of 50 nM and the chamber was allowed to equilibrate for 10 minutes. The entire chamber was mounted on the confocal microscope and examined with a 60× objective connected to a Z series motor. One mL of a CCCP solution (total concentration 10 μM and, in some cases, containing 50 nM TMRM) was added to the cell chamber and a timer started. A series of images (1 to 2 μm in thickness) was taken in the vertical plane 15 seconds after addition of the CCCP solution, and then every minute for the first 10 minutes. Images were taken at 5 minute intervals thereafter until the 30 minute time point. Cells were illuminated at 488 nm and the fluorescent images were collected at 600 nm (50 nm band pass) and 700 nm (50 nm band pass) for the first two channels. The third channel for TMRM had a 568 nm excitation and an emission of 600 nm (50 nm band pass). Cells loaded with TMRM only, NOVs only, NOV matrix without dye (blank), free dye in water (at the same final concentration delivered in the NOV) or untreated cells provided the panel of controls used in the validation of the NOV. In some cases, the final polymer coating was not applied and the loaded NOVs added directly to the cells.

Repeat depolarizations were performed as follows. Astrocytes were prepared as above, but the cell chamber only contained 500 µL of HBSS with HEPES. 500 µL CCCP (5 µM final concentration in chamber) was added and images were collected every minute for the first 10 minutes after the addition of CCCP and every 5 minutes thereafter until the 45 minute time point. Then 500 µL of the CCCP solution was added at the 46 minute time point, and the images taken every minute until the 55 minute time point and every five minutes until the 90 minute time point.

Image analysis was performed as follows. Images were transferred to the MetaMorph image analysis package and regions of interest chosen consistent with TMRM-induced mitochondrial fluorescence, or the autofluorescent mitochondria of the astrocytes. In some cases, the images were expanded and regions of interest (ROI) were also chosen from the surrounding cytosol. The average pixel intensity ratio of the 600 nm image versus the 700 nm image was then calculated. For the TMRM channel, the average pixel intensity was recorded.

Figure 5:
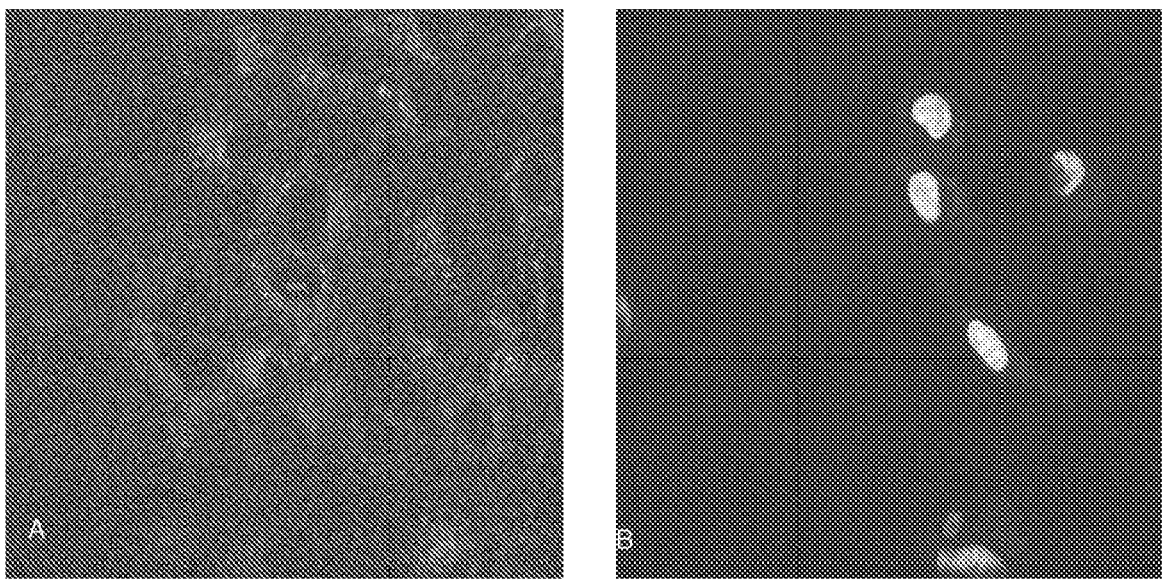
FIG. 5 shows C6 glioma cells that have been incubated with particles having different coatings.

Localization of the NOV was performed as follows. FIG. 5 shows C6 glioma cells that have been incubated with particles that have different coatings. Particles with a positive polymer layer are distributed throughout the cytosol, but are excluded from the nucleus. In contrast, particles that do not have a positive coating are almost exclusively found in the nucleus suggesting cellular trafficking as the primary mode of transport. These results demonstrate how the particles may be selectively targeted to different regions of the cell, simply based on the exterior coating of the particles. Other surface modifications could include a coating of positively charged biomolecules such as poly(lysine) to further enhance interactions with cells. In addition, modifications using a different capping silane that would allow for the attachment of targeting biomolecules could also be used to selectively direct the particles to different organelles or other regions of the cells. As a side note, uncoated particles, although localizing to the nucleus, also appeared to be more cytoxic than the coated particles, with invagination and crenellation of the cell membrane, rounding of the cell, loss of substrate adhesion and concomitant cell death.

Figure 6:
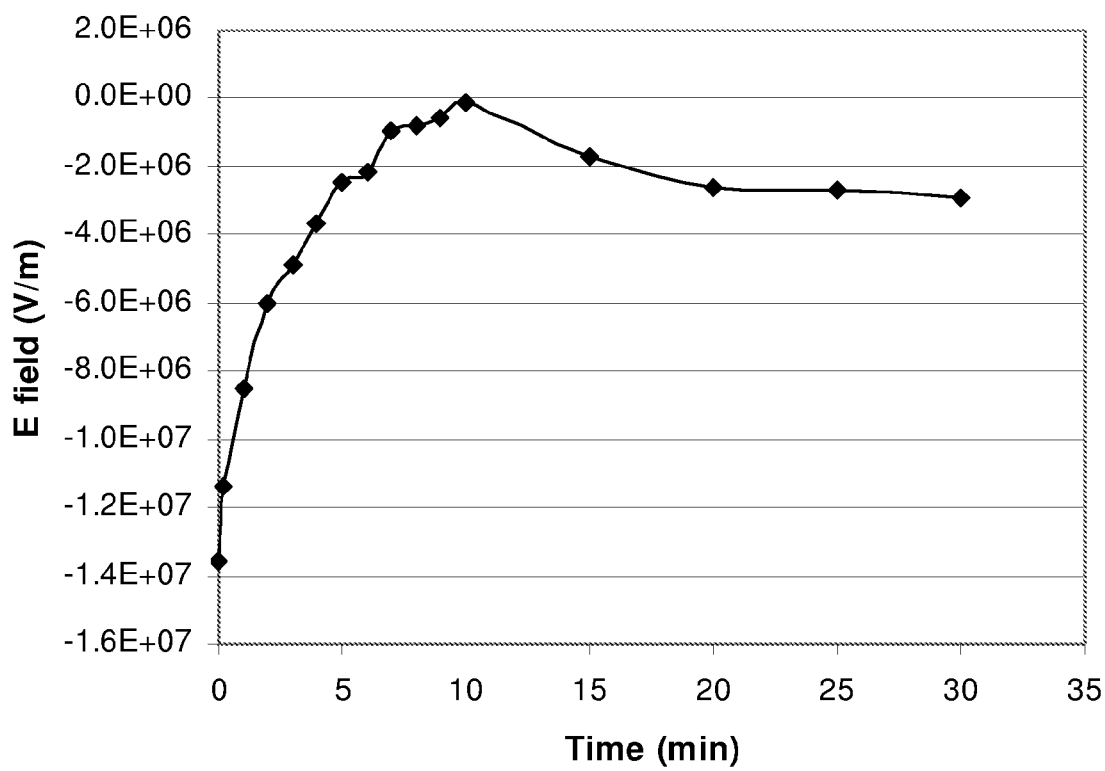
FIG. 6 is a graph illustrating the depolarization curve extracted from the NOV emission ratio.

CCCP depolarization was performed as follows. C6 gliomas incubated with the NOV and TMRM to visualize mitochondria were depolarized with CCCP. FIG. 6 shows the depolarization curve extracted from the NOV emission ratio. A region of interest was first determined in Metamorph by the punctuated bright areas that indicated mitochondria through TMRM localization. The emission ratio was then determined at the measurement time points. A reference emission ratio was determined from an area that did not contain a cell, but had fluorescent intensity (residual NOV stuck to the cover slip). This reference point was used as E field=0, and was the value used to calculate $\Delta R/R$. Once the measurement was converted to $\Delta R/R$, the values extracted from the external calibration curve were used to determine the E field at the region of interest.

For the example given, at time zero, before the addition of CCCP, the mitochondrion should be fully polarized. The E field value is $-1.4\times10^7$ V/m, which corresponds closely to a normal, polarized mitochondrion. After the addition of CCCP, the E field quickly decreases and approaches zero in the span of approximately 10 minutes. There is then a slight repolarization of the mitochondrion. This experiment demonstrates the ability of the NOVs to follow fluctuations in the E field produced by a cellular component, in this case mitochondria.

Cells exposed to free dye in water did not fluoresce, providing compelling evidence that the dye must be incorporated into the nanoparticles in order to be taken up by the cells. Control NOV with no dye incorporated into the particles, or cells with nothing added to them, did not show meaningful traces. Cells with only TMRM added showed a typical slow-response dye depolarization curve (data not shown).

Comparison to TMRM and other E field methods was performed as follows. TMRM was used to locate the mitochondria for analysis, but it may also be used to estimate changes in the mitochondrial membrane potential with the following formula modified from Plasek et al:

$$\Delta\Psi=58.7\ \log(I_2-I_{2B}/I_0-I_{0B}).$$

Here $I_0$ is the average pixel intensity in the mitochondrial region of interest at time zero (before addition of CCCP) and $I_{0B}$ the average pixel intensity at a region of interest inside the cell, but not located on a mitochondrion at time zero. The background fluorescence is comprised of the cell's natural autofluorescence, the NOVs, and the TMRM as it leaks out of the depolarized mitochondria. $I_2$ and $I_{2B}$ are the subsequent average pixel intensities for the mitochondrial and control region of interest, respectively. The change in mV is then converted to changes in E field, assuming a mitochondrial membrane thickness of 5 nm.

Figure 7:
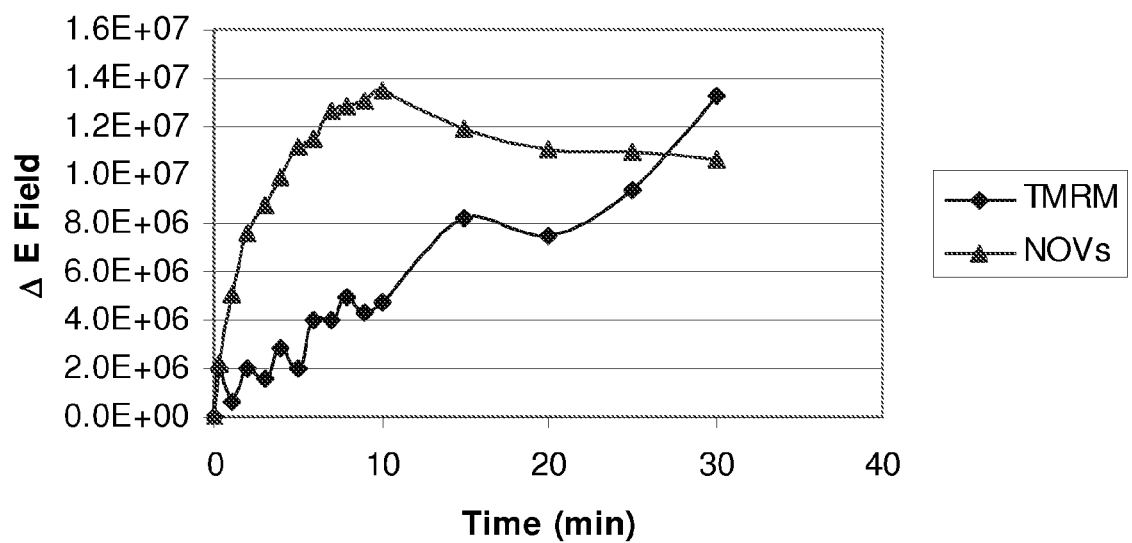
FIG. 7 is a graph illustrating the change in E field as determined by the NOV and the TMRM methods.

FIG. 7 shows the change in E field as determined by the NOVs and the TMRM method. Both traces show a large change in E field, but the NOVs reach their maximum change more quickly than seen by the TMRM method. In addition, the NOVs show a slight repolarization of the mitochondrion. These results are consistent with the two systems. TMRM is a slow response dye, physically translocating across the membrane. Indeed, depending on concentration and local conditions, the dye may take several minutes to respond to significant changes in E fields. Di-4-ANEPPS, however, is a fast response dye, taking milliseconds to respond to relatively small shifts in local E fields. The NOVs have been used successfully to track the depolarization and subsequent repolarization of respiring mitochondria in situ, while TMRM in the same preparation lags behind in recording the identical change in E field (FIG. 7). The two traces verify that the di-4-ANEPPS maintains its fast response properties, even though it is embedded within the matrix of the nanoparticles. The fast response property of the particles will thus allow the identification and isolation of rapid fluctuations in the mitochondrial membrane potential, and will provide a substantial increase in the ability to measure faster temporal changes in a variety of other cellular and non-biological systems.

Figure 8:
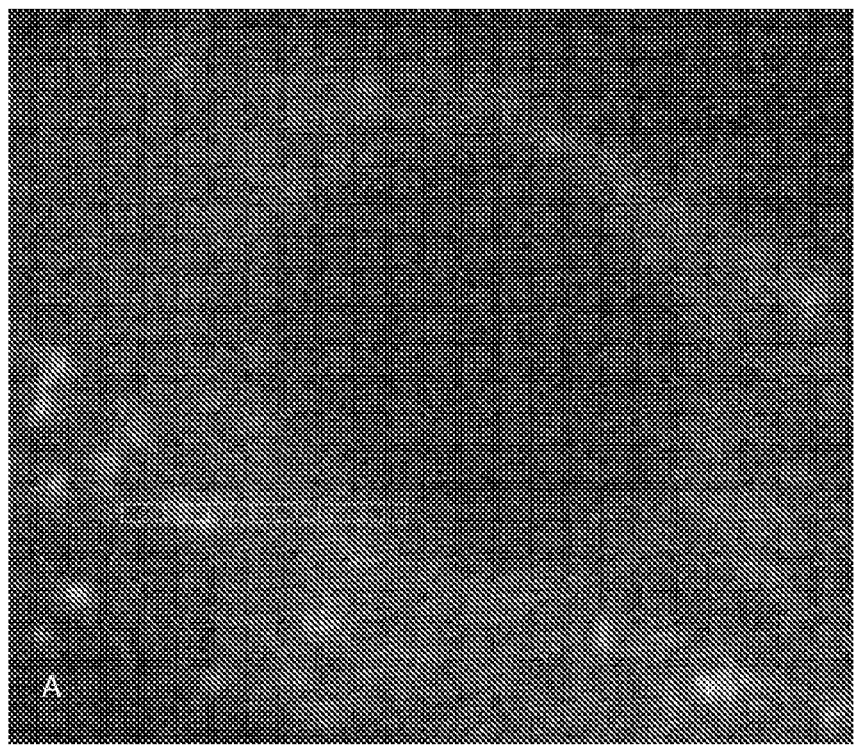
FIG. 8 shows the change in E field in a region of interest as a function of distance from the mitochondrion.
Figure 8:
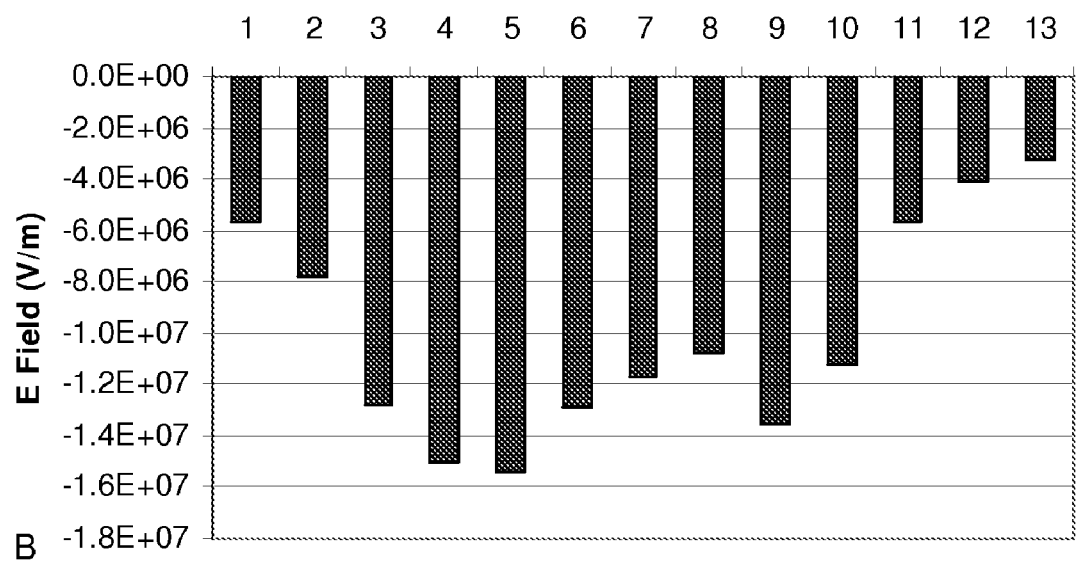

Cytosol measurements were made as follows. FIG. 8 shows the change in E field in a ROI as a function of distance from the mitochondrion (regions 3-5). The E field drops significantly and rapidly with distance from the polarized mitochondrial membrane. However, the spatial picture is complicated by the presence of mitochondria outside the plane of analysis. As the ROI cross another, out of plane, mitochondrion (regions 9-10), the E field again increases and then drops off towards zero as the regions extend into the cytosol and toward the nucleus. However, the E field intensity never achieves the maximal intensity measured for the in-plane mitochondrion. This further confirms the usefulness of the NOV in the mapping of three-dimensional E fields in cytosol and membranes: a feat not readily attained using existing techniques.

In addition to the effects of neighboring mitochondria, there may also be stray E fields in the cytosol that previously were not amenable to measurement. This result demonstrates the ability of the nanoparticles to measure electric fields outside of the lipid bilayers. All of the voltage dye and patch clamp technique measurements are constrained to the membrane domains. Current techniques, including all clamps or optical dyes, are not able to determine electric fields in the cytosol or other non-membrane regions. If microelectrodes are used to measure non-membrane bound potentials, they must first puncture the external membrane. In addition, the electrodes do not have the ability to measure multiple regions simultaneously. The present disclosure significantly increases the amount of electric field information that may be obtained from cells. In addition, using the NOV in conjunction with confocal microscopy will allow three-dimensional imaging of E field gradients throughout an entire cell or external region. Such contour maps will greatly enhance knowledge of how E fields modulate cellular activities.

Sequential depolarizations were performed as follows. Astrocytes with autofluorescent mitochondria (to eliminate the need for TMRM) were incubated with NOVs, transferred to a confocal microscope, and the mitochondrial membrane depolarized with the use of CCCP. The mitochondria were then allowed to slightly repolarize, and a second dose of CCCP was applied.

Figure 9:
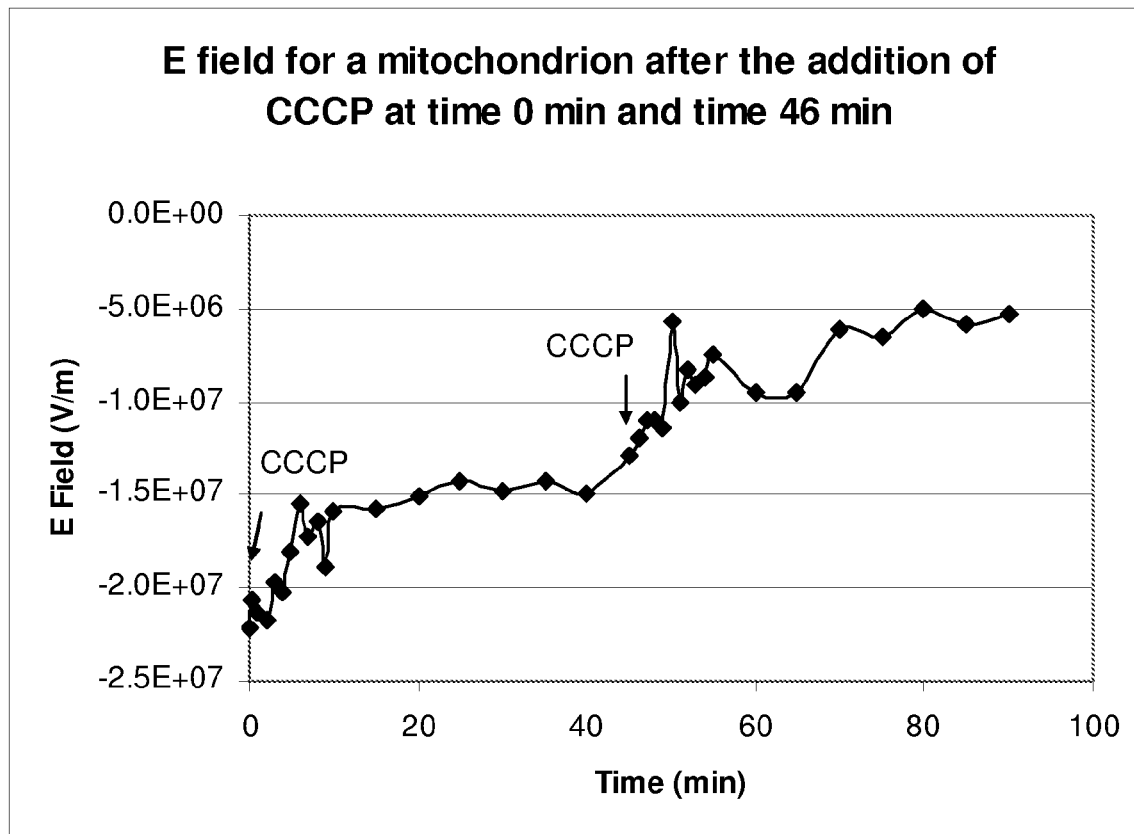
FIG. 9 is a graph illustrating the E field over time for a sequentially depolarized autofluorescent mitochondrion as monitored by NOVs.

FIG. 9 shows the E field over time for an autofluorescent mitochondrion as monitored by NOVs. As before, there is a decrease in the E field during the first 10 minutes, and then a leveling out of the E field. More CCCP is added at the 46 minute time point, and there is again another sharp decrease in the E field with a subsequent leveling out of the E field. This result demonstrates the NOVs' ability to track multiple changes in the E field during a time course experiment.

EXAMPLE 4

Dye Loading of NOV

Concentration was determined as follows. A known volume of the NOV synthesized in Example 1 was placed in a pre-weighed vial. The contents were allowed to air-dry for three days. The vial was then re-weighed and the concentration of solid material determined. There were ~5 mg of particles/mL.

Maximum dye loading was determined as follows. Di-4-ANEPPS (0.3 mg) was dissolved in 3 mL chloroform and used as a stock solution. In dram vials, 500 µL of emulsion was placed. Increasing amounts of the di-4-ANEPPS stock solution was added to the dram vials. The solutions were sonicated for 30 seconds, and then stirbars were added and the solutions stirred under an Al foil tent for 30 minutes (until the solutions were clear). The solutions were filtered through a 0.2 micron filter and analyzed on either a Molecular Devices Spectramax Gemini XS (excitation 490 nm, emission 500-800 nm with 5 nm steps), or a Molecular Devices Spectramax 384plus (350-750 nm with 10 nm steps).

The fluorescence intensity (monitored at 650 nm) or absorbance (monitored at 470 nm) was plotted versus dye concentration. Where the intensity began to level off was considered the maximum loading for the dye, and a slightly lower value was used to load the nanoparticles (~1 µg of dye/mL emulsion).

Leaching was determined as follows. For uncoated silane capped microemulsions, 20 mmol HEPES was added to 3 mL of loaded NOV emulsion and 3 mL of 2× Hanks Balanced Salt Solution and briefly stirred. Two milliliters of the NOV solution was then transferred to a 3.5 kDa MWCO SpectraPor cellulose ester dispodialyzer and the membrane placed in a dark plastic bottled containing 300 mL 1×HBSS and 10 mmol HEPES. The solution was stirred slowly and the bath water was checked every hour for 9 hours, and then at 24 hours. There was no apparent leaching of the dye into the bath solution Photobleaching was determined as follows. For uncoated silane capped microemulsions, a small dot of the dried, loaded emulsion was placed onto a glass cover slip and constantly illuminated at 488 nm (0.628 mW). Images of the dot were taken every minute for 15 minutes at both 600 nm (50 nm band pass) and 700 nm (50 nm band pass) emission wavelengths. There was a 10% decrease in the emission ratio after 15 minutes of constant exposure. Using an exposure time of 100 msec, it would take 9000 measurements before there was a 10% decrease in the emission ratio.

EXAMPLE 5

Synthesis of E-PEBBLEs, Controls, and Calibration

All chemicals, unless noted, were purchased from Sigma-Aldrich (St. Louis, Mo.). Triton X-100 (0.625 g, 1 mmol) was dissolved in 10 mL of deionized water. Octyltriethoxysilane (63 µL, 0.2 mmol) was slowly added and the solution allowed to stir for 30 minutes. Ammonium hydroxide (10-20 µL of a 2.2 M solution) was added, and the solution was stirred for 72 hours. Trimethylethoxysilane (200 µL, 1.3 mmol) was added, and the solution allowed to stir for an additional 48 hours.

The solution was dialysized against water for 24 hours in a Spectra/Por polyvinylidene difluoride (PVDF) dialysis membrane (Spectrum labs, Rancho Dominguez, Calif.) with a 250 kDa molecular weight cut-off. The bath water was changed 3× during the 24 hour period. The particle solution was then stirred with an equal volume of a 1 wt % solution of poly (diallyldimethylammonium chloride) (low molecular weight) and again dialyzed for 24 hours. Cleaned emulsions were placed on a holey carbon coated grid (SPI Supplies, West Chester, Pa.), allowed to dry, and analyzed through transmission electron microscopy (JEOL 3011 High Resolution Electron Microscope). Solutions of E-PEBBLEs were also analyzed with light scattering using the number weighted distribution (PSS Nicomp 380 ZLS, Particle Sizing Systems, Santa Barbara, Calif.).

A 2 mL aliquot of the washed and coated particles was sonicated with a 20 µL solution of di-4-ANEPPS (Molecular Probes, Eugene, Oreg.) dissolved in chloroform (0.1 mg/mL, 0.2 mM). A stirbar was added and the solution was stirred under an aluminum foil tent for 30 minutes to remove the chloroform. Solutions were stored in the dark at room temperature and calibrated through use of an external calibration device. Unless otherwise stated, the E-PEBBLEs are used dispersed in the above aqueous stock solution with a concentration of ~5 mg nanoparticles per mL.

E-PEBBLE controls were performed as follows. E-PEBBLE controls were examined in a Horiba Fluoro-Max-3 (excitation 488 nm, emission 500 nm to 800 nm, slits 5.00 nm). Emission ratios were constructed by averaging the fluorescent intensity for 50 nm wide regions. For example, to obtain the 600 nm data point, the average intensity between 575 nm to 625 nm was calculated. Emission ratios analyzed were 600:700 nm, and 525:700 nm. Emission spectra of free dye dissolved in organic solvents were taken using approximately the same concentration of dye as found in the loaded nanoparticle solution.

To assess the possibility of reactive oxygen species affecting the E-PEBBLEs performance, the following protocol was followed: A solution of E-PEBBLEs (100 μL stock solution in 3 mL di water) was placed in a plastic cuvette and the emission spectrum determined. Hydrogen peroxide (100 μL of a 30 wt % solution, GFS Chemicals, Columbus, Ohio) was added to the cuvette, and the liquid was pipetted to disperse the E-PEBBLEs. An emission scan was taken immediately and then every five minutes thereafter for 15 minutes.

The E-PEBBLE's response to different pH solutions was also measured. E-PEBBLEs (50 μL stock solution) were placed into plastic cuvettes. Fisher Buffer Solutions (Fisher Scientific, Hampton, N.H.) ranging from pH 5 to pH 9 were added to the cuvettes, and the solutions pipetted to disperse the nanoparticles. Emission spectra were taken for each pH.

The effect of different concentrations of dissolved oxygen on the E-PEBBLE's performance was examined as follows: To an air-tight quartz cuvette fitted with a septum and cap, 50 μL E-PEBBLEs stock solution was added along with 3 mL deionized water. $N_2$ (pre-purified, Metro Welding, Detroit, Mich.) was bubbled through the solution for 10 minutes, the cuvette was then sealed, and the emission spectrum recorded. Oxygen (USP, Metro Welding, Detroit, Mich.) was then bubbled through the solution for 4 minutes, followed sequentially by air (dry grade, Metro Welding, Detroit, Mich.) for 10 minutes, $N_2$ for 10 minutes and $O_2$ for 10 minutes. Emission spectra were taken after each exposure to the gas.

The E-PEBBLEs were also examined to determine if the voltage sensitive dye leaches out of the nanoparticle matrix over time. A solution of E-PEBBLEs (1.5 mL stock solution) was placed into PVDF dialysis tubing (250 kDa MWCO) and the tubing placed into a 300 mL water bath. The bath water was gently stirred. Aliquots of the bath water solution were taken after 15 seconds of incubation, and then every hour thereafter for 7 hours. Aliquots were placed in a plastic cuvette and measured in a Horiba FluorMax-3 spectrofluometer (parameters as above but with slits of 2.5 nm). After the fluorescent measurement, the aliquot of the bath solution was returned to the bath. After the seven hour time point, an aliquot of the bath water was mixed in a 50:50 ratio with 95% ethanol (AAPER, Shelbyville, Ky.), to ensure that dye molecules were not leaching from the nanoparticles and forming insoluble and non-fluorescent aggregates. The contents of the dialysis tube were then emptied into the bath solution and stirred to provide the maximum possible fluorescent intensity for the bath solution.

The effect of temperature on a solution of E-PEBBLEs was examined as follows: A solution of E-PEBBLEs (150 μL stock in 3 mL) was placed in a pre-heated chamber containing a glass coverslip bottom. Temperature measurements and corresponding emission spectra were taken approximately every minute as the solution heated to over 37° C. The chamber was then allowed to cool, and the temperature and emission spectra were again taken until the solution reached room temperature. Emission spectra were taken on an Olympus IMT-II (Lake Success, N.Y., USA) inverted fluorescence microscope with an Acton Research Corp. (Trenton, N.J.) spectrograph and a Hamamatsu (Hamamatsu, Japan) HC230 charge-coupled device (CCD) interfaced with an Intel Pentium computer. The CCD was controlled by the software program LABVIEW (National Instruments, Austin, Tex.). Excitation was from a Xenon lamp, and the microscope was fitted with standard Olympus blue filter cube. Emission ratio values taken during the heating portion of the experiment are labeled with a "h." Those values taken during the cooling period are labeled with a "c."

A calibration device was fabricated as follows. Square glass capillary tubes (inner diameter of 52 microns and an outer diameter of 300 microns) (Polymicro Technologies, LLC, Phoenix, Ariz.) were stripped of their polyimide coating by soaking in concentrated sulfuric acid at 150° C. for 5 minutes. The stripped tubes were then soaked in deionized water for 30 minutes and finally soaked in 95% ethanol for 30 minutes. The tubes were allowed to dry overnight.

The stripped tubes were cleaved into small pieces (~5 mm in length) and loaded with E-PEBBLEs synthesized in Example 5 by dipping the ends of the tubes into either a solution of the E-PEBBLEs or a dried gel of the nanoparticles. The loaded tubes were affixed to glass cover slips with a thin, clear varnish (Revlon clear 771, Revlon, New York, N.Y.). The varnish was allowed to dry for 30 minutes before the sides of the tube were painted with silver paint (SPI Supplies, West Chester, Pa.) and allowed to dry overnight. FIG. 11A shows a schematic of the external calibration device.

External calibration of E-PEBBLEs was performed as follows. Safety note: Arcing and electrical shock are possible at this step. Appropriate measures to guard against fire and electric shock should be in place before the power supply is connected. The calibration device fabricated above was fixed to the stage of a confocal microscope (Olympus IX70 connected to a Life Science Resources (Cambridge, UK) Ultra-View equipped with an Ar—Kr laser and a Lambda 10-2 Sutter wheel from Sutter Instrument Co. (Novato, Calif.)). Wires were connected to the device by painting them to each side of the capillary tube with silver paint. The wires connected to a power supply (PowerPac HV, Bio-Rad Laboratories, Hercules, Calif.), and the electric field modulated through the use of the power supply. Voltages were increased by 250 V steps until 0 V. The voltage for each data point was allowed to stabilize for 1 minute before taking a measurement. The power supply was then allowed to rest at 0 Volts for 1 minute before a new voltage was entered. Devices were not exposed to voltages >1250 V. After this voltage, the devices experienced arcing or shorts in the system. The E-PEBBLEs were excited at 488 nm. Emission images were collected at 600 nm (50 nm band pass), 700 nm (50 nm band pass), and 525 nm (50 nm band pass) with Perkin Elmer (Foster City, Calif.) UltraView imaging software in Temporal mode.

Figure 11:
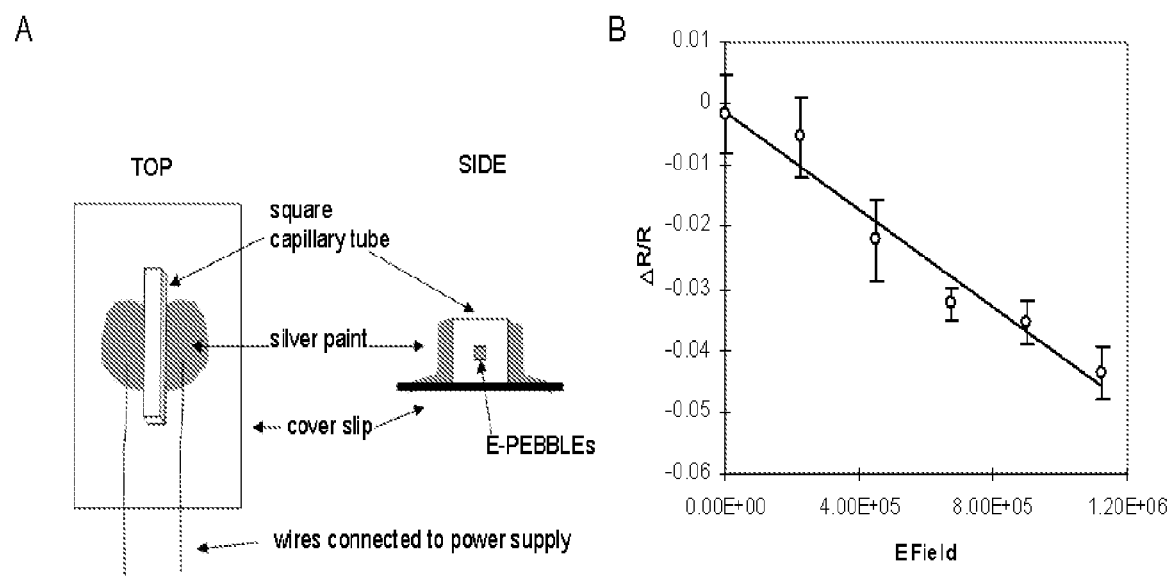
FIG. 11 panel A is a schematic for an external calibration device and panel B graphically depicts a calibration curve for E-PEBBLEs.

Calibration image analysis was performed as follows. Images were transferred to the image analysis package Meta-Morph (Molecular Devices, Sunnyvale, Calif.), and rectangular regions of interest (ROI) were chosen spanning the length of the capillary channel, both on the positive and negative sides of the channel. Regions that were noticeable (brighter areas or regions at the edge of a feature) were also selected for analysis. The average pixel intensity for each ROI was calculated. The emission ratio (R) was then determined using the average pixel intensity values for the 600 nm emission image versus the 700 nm image, or the 525 nm emission image versus the 700 nm emission image. The emission ratio was plotted versus electric field. As the glass sliding of the capillary tube will diminish the E field across the microchannel where the E-PEBBLEs are located, the E field was calculated by taking the E field at 200 microns (step voltage divided by the width of the capillary tube) and dividing by the dielectric constant of the silica (3.7) as reported in the product literature (31). To eliminate any background fluorescence from the measurements, a "change in ratio" (subtracting the ratio (R) at a given E field from the ratio when no E field is present and dividing by R (ΔR/R) was also calculated and plotted versus electric field. At least four trials were completed (two curves with the E field increasing and two curves with decreasing E fields) and used to provide the arithmetic mean and standard deviation prior to the performance of regression analysis to determine the slope, intercept, and errors of the calibration curve. These values for slope and intercept were used when analyzing cellular systems. A representative calibration curve is shown in FIG. 11 B.

Figure 10:
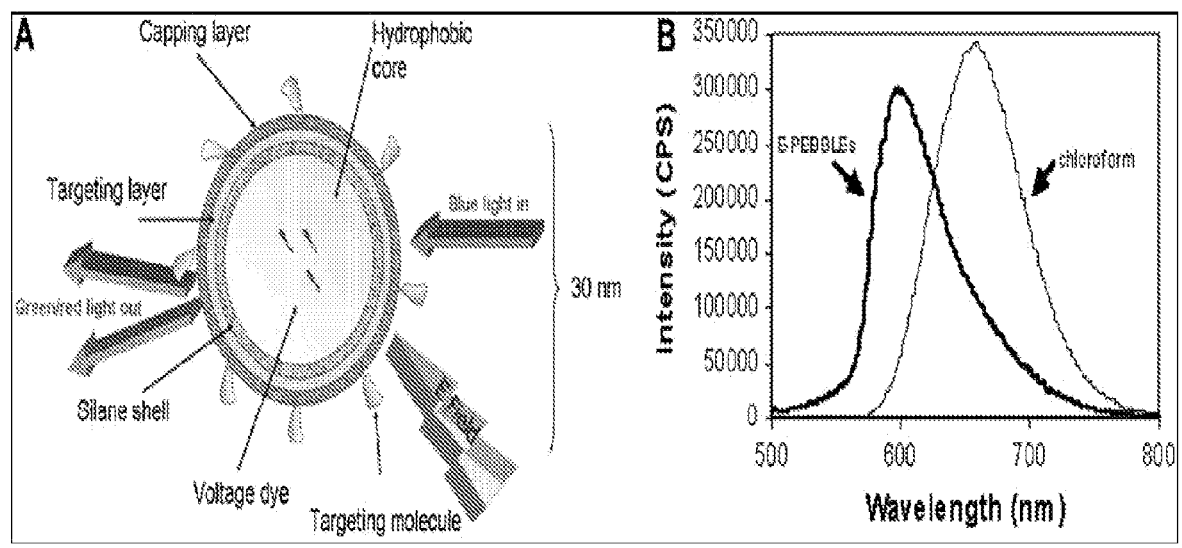
FIG. 10 panel A is a schematic of an E-PEBBLE and panel B graphically depicts an emission spectrum from an aqueous suspension of E-PEBBLEs.
Figure 12:
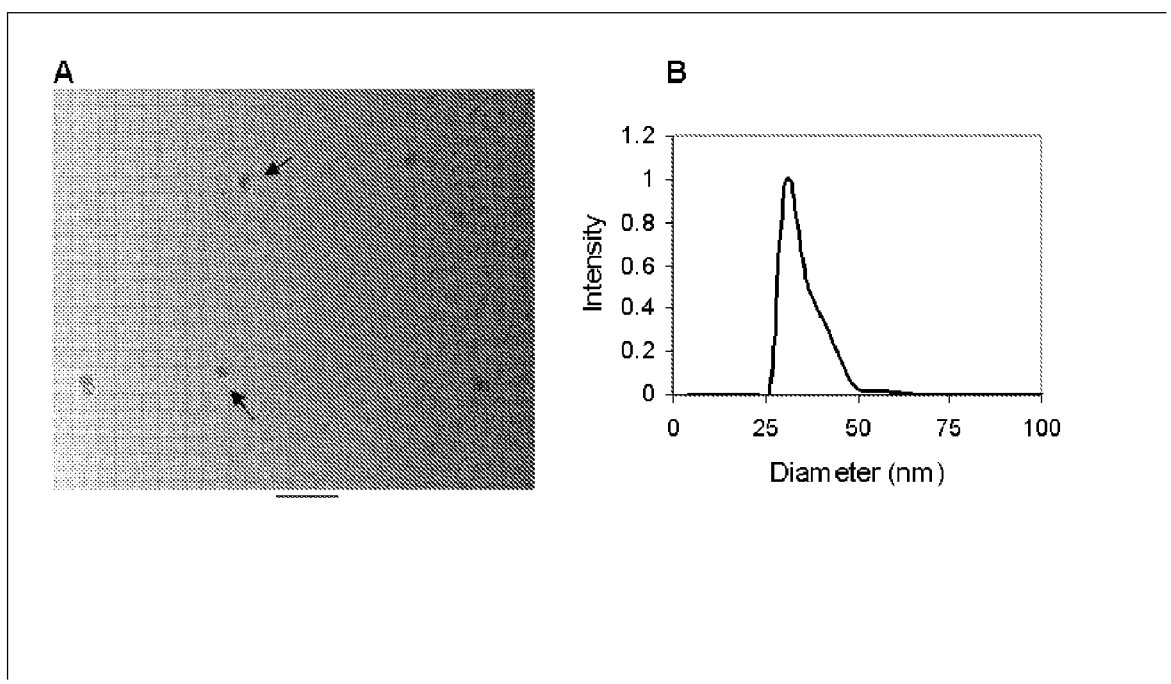
FIG. 12 panel A is a transmission electron microscopy image of E-PEBBLEs, with the scale bar equal to 100 nm, and panel B graphically depicts the number weighted light scattering data for E-PEBBLEs.

Results of the synthesis of E-PEBBLEs and E-PEBBLE controls are summarized as follows. The nanosized sensors are composed of silane capped mixed micelles that contain the ratiometric, fast response voltage dye di-4-ANEPPS (FIG. 10 A). The particles contain a hydrophobic core comprised of the organic chains of the organo-silanes. The micelle is stabilized by polymerizing the silane headgroups. A monoethoxysilane is then added, capping off any unreacted silane groups to prevent aggregation of the particles. Additional silane or polymer layers may be added for enhanced targeting or biocompatibility of the particles. The voltage dye is encapsulated into the organic core of the particle, where it is stabilized in a uniform environment, allowing for universal calibration. Nanoparticles excited at 488 nm produce a broad emission spectrum, ranging from 500 nm to 800 nm, with the emission peak blue shifted from that of the free dye dissolved in chloroform (FIG. 10 B). In addition, the emission spectrum narrows as the dye molecules enter the particle (~15 nm less than the corresponding free dye in chloroform, full width half-maximum). Although not strictly mono-disperse, E-PEBBLEs have a mean hydrodynamic diameter that is fairly tightly distributed around 30 nm as determined by transmission electron microscopy (FIG. 12 A) and light scattering (FIG. 12 B).

The particle solution dries to a gel, and either the aqueous suspension or the gel itself is placed into an external calibration device. The E field the particles are exposed to may be modulated through use of a power supply connected to the external device by wires. As the E field experienced by the nanoparticles increases, the emission ratio (calculated from the emission intensity at 525 nm and 700 nm, excitation 488 nm) of the embedded dye decreases. The raw curves are then transformed into "change in emission ratio over emission ratio" (ΔR/R), by subtracting the emission ratio at a certain E field from the emission ratio when there is no E field present and the slope and y intercept calculated using regression analysis with 95% confidence ($r^2$=0.96, significance F=0.0006). The slope and y intercept for the batch of E-PEBBLEs used in this experiment was $-3.9 \times 10^{-8}$ V/m and −0.001, respectively. These values from the external calibration are then used to determine the E fields inside cells, without having to calibrate individual sensors within the cells themselves. Regions of interest (ROIs) from both the positive and negative sides of the channel inside the calibration device are examined as well as any other noticeable feature (i.e. bright portions of the tube). There does not appear to be any migration of the nanoparticle gel, either in the form of uneven changes in fluorescent intensity or movement of the gel out of the ROI, during the application of the E fields, indicating that the optical response arises solely from the electrochromatic changes of the dye itself.

Figure 13:
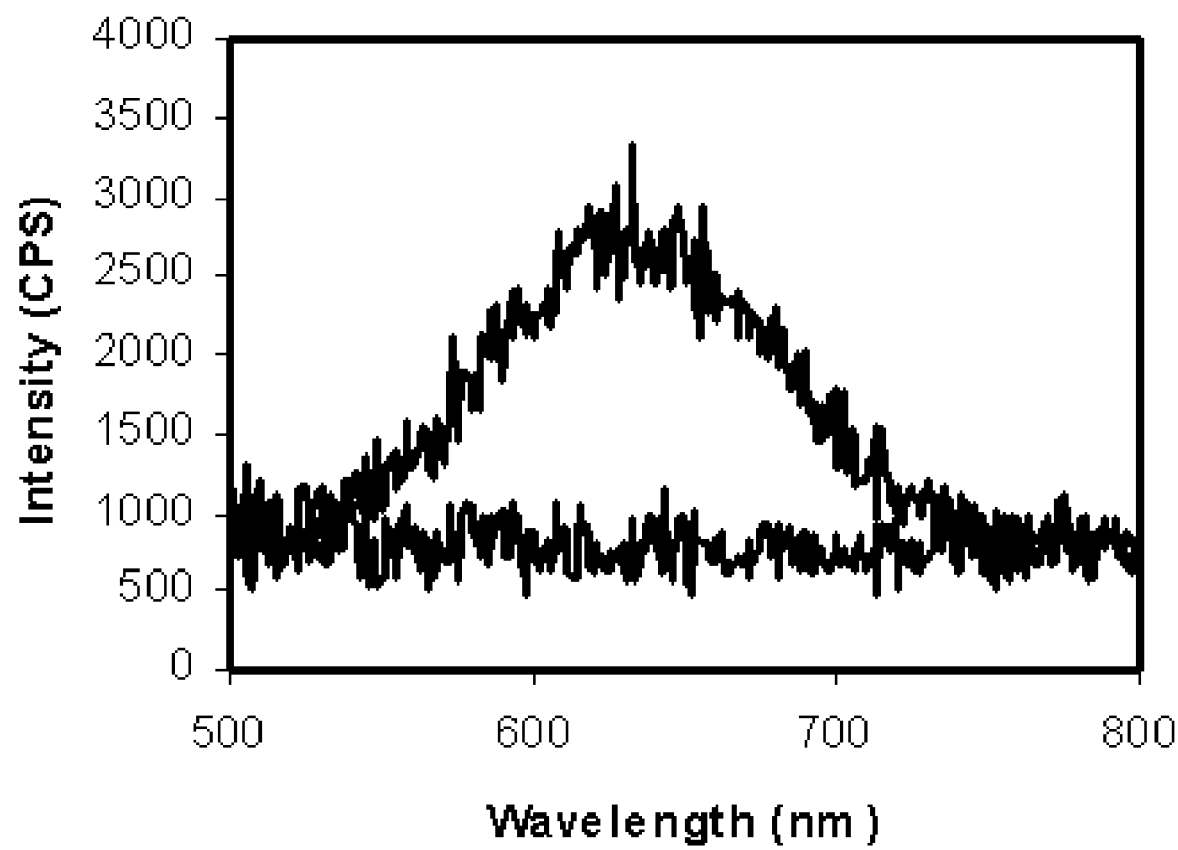
FIG. 13 graphically depicts the emission spectra from a water bath exposed to a dialysis tube containing stock E-PEBBLEs.

E-PEBBLEs exposed to hydrogen peroxide, a range of pH solutions, or varying oxygen concentrations, showed no noticeable change in the corresponding emission ratios (data not shown). E-PEBBLEs incubated in a water bath for seven hours showed no evidence of the dye molecules leaching out of the nanoparticles (FIG. 13). Adding ethanol to the bath water to probe for insoluble and non-fluorescent aggregates produced no fluorescent response.

Figure 14:
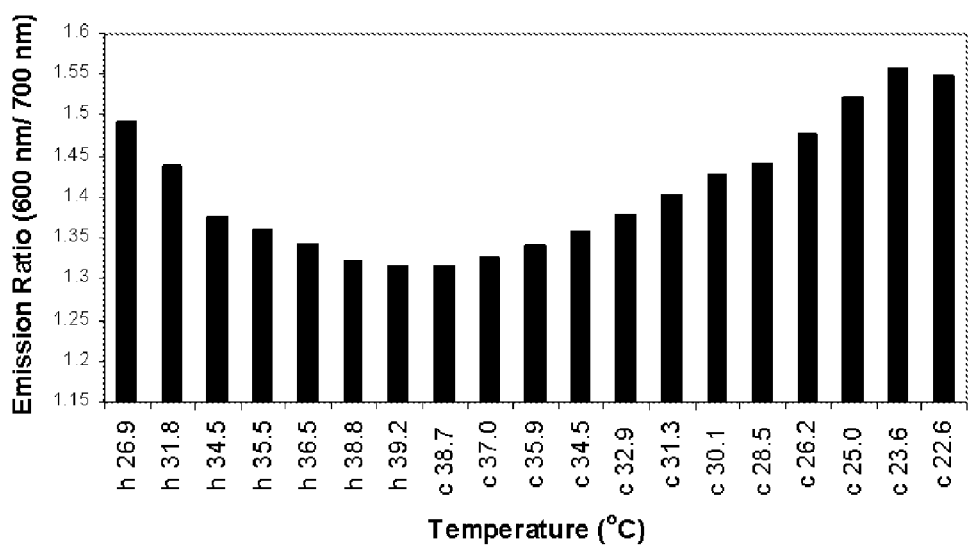
FIG. 14 graphically depicts the partial temperature dependence of E-PEBBLEs for heating (h) and cooling (c) cycle of an E-PEBBLE solution; with panel A showing emission ratio of 600 nm/700 nm; panel B showing emission ratio of 525 nm/700 nm for the same data set; and panel C comparing fluorescent spectra taken at 35° C. and 27° C.
Figure 14:
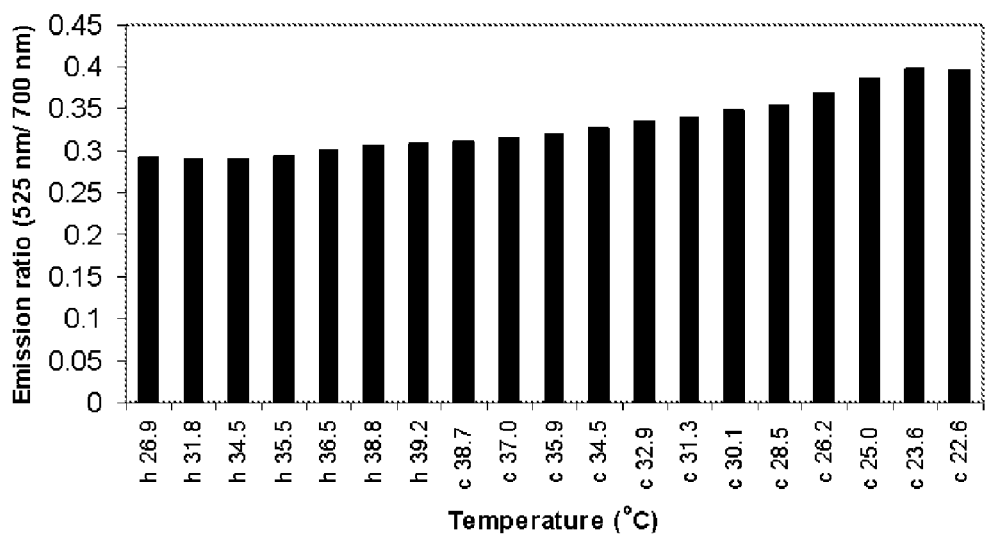
Figure 14:
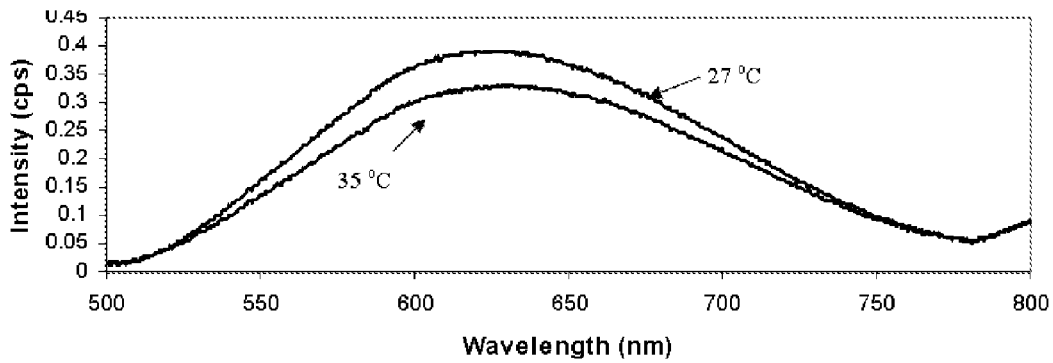

Monitoring the emission ratio of 600:700 nm, a reversible temperature dependence was found for the E-PEBBLEs. This emission ratio reversibly decreases with increasing temperature (FIG. 14 A). However, using a different portion of the broad emission spectrum eliminates the temperature effects. The emission ratio of 525:700 nm does not show any temperature dependence (FIG. 14 B). There is only a slight increase of the emission ratio over the time course of the experiment, most likely due to the evaporation of water and the subsequent concentration of the E-PEBBLE solution. FIG. 14 C compares the fluorescent spectra of the E-PEBBLE solution at 35° C. and 27° C.

Although the calibration curve does not extend into the highest regions of cellular E fields, it is expected that the E-PEBBLEs will maintain their linearity throughout the cellular E field range. Studies on the linearity of di-4-ANEPPS or a structurally similar dye (di-8-ANEPPS) show that the emission ratio produces a linear response from $-2.4 \times 10^7$ V/m to $1.2 \times 10^7$ V/m in a variety of environments, ranging from isolated neurons to intact hearts.

There is an ~0.04 change in the emission ratio from 0 V/m to $1.13 \times 10^6$ V/m. Knisley et al. report an; 0.001 change in ratio per $1.13 \times 10^6$ V/m (assuming a linear calibration curve) for free dye embedded in the heart tissue. This larger change in the E-PEBBLEs emission ratio is likely due to the absence of cellular artifacts or internalization of the free dye by the cell.

Notably, the E-PEBBLEs were found to be insensitive to pH, $O_2$ gradients, or reactive oxygen species (as tested by $H_2O_2$). The leaching studies indicate that the dye remains in the hydrophobic core of the nanoparticle, thus providing a sensor that is stable over the lifetime of the cellular experiment in various environments.

Figure 16:
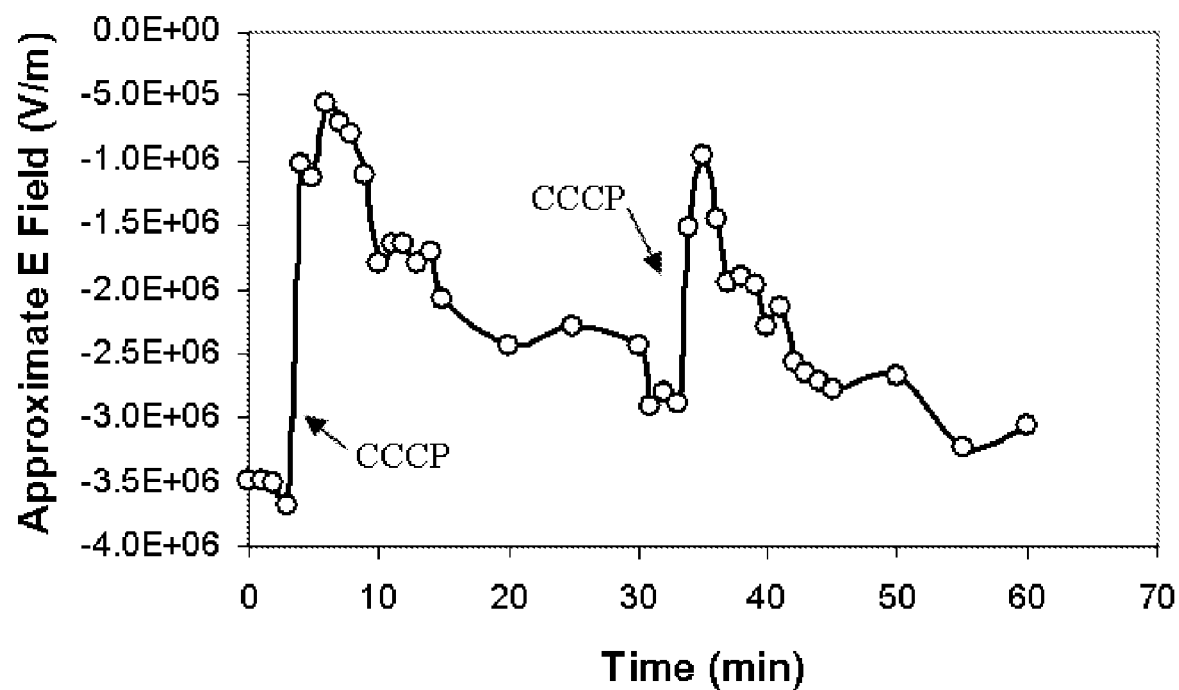
FIG. 16 graphically depicts multiple E field changes after CCCP is added at time 3 minutes 50 seconds and time 33 minutes 50 seconds (arrows), where a rapid loss of the E field associated with a mitochondrial region is observed, followed by a modest repolarization.

E-PEBBLEs containing di-4-ANEPPS can be temperature sensitive, depending on the portion of the fluorescent spectrum utilized (FIG. 14). Such temperature-dependent phenomena have also been observed for excitation ratios of several voltage-sensitive dyes. A temperature dependence has been noted for di-8-ANEPPS, a structurally similar dye to di-4-ANEPPS, near the emission maximum of the molecule (~580 nm). By utilizing the very broad emission spectrum of di-4-ANEPPS (FIG. 10 B), temperature-insensitive emission ratios may be formed. Specifically, using an emission ratio of 525:700 nm eliminates any temperature dependence from the E field measurements. As an experiment may be devised to encompass both the temperature-sensitive and temperature-insensitive regions of the E-PEBBLEs spectrum, there arises the possibility of using the E-PEBBLEs as both E field and temperature sensors simultaneously. Even though parts of the emission spectrum are temperature sensitive, these emission ratios may still be utilized to determine relative changes in the E field (FIG. 16). Alternatively, if the temperature is kept constant, E field values may be extracted from the temperature-sensitive regions by first taking into account the temperature effect on the emission ratio. There are some advantages to using the 600:700 nm emission ratio. Since the 600:700 nm emission ratio is constructed using emission intensities taken from the top and side of the fluorescent emission peak, there is more fluorescent intensity and a lowering of the signal/noise ratio. As a result, the data obtained from the 600:700 nm ratio, although temperature sensitive, tend to be less noisy than the data extracted from the temperature-insensitive data of the 525:700 nm emission ratio, which is constructed using emission intensity from the sides of the emission peak. If the temperature of the experiment is carefully controlled, or if only relative changes in the E field are desired, the 600:700 nm selection is a convenient emission ratio to use.

EXAMPLE 6

Methods of Using E-PEBBLEs to Measure Cellular E Fields

Mitochondrial membrane and cytosol potentials were measured as follows. Immortalized rat (DITNC) astrocytes with autoflourescent mitochondria (American Type Culture Collection, Manassas, Va.) were plated on to glass cover slips at a concentration of ~2×$10^5$ cells/mL. Cells were incubated in Dulbecco's Modified Eagle Medium (DMEM) supplemented with 10% fetal bovine serum and 1% penicillin/streptomycin (Invitrogen, Carlsbad, Calif.) overnight. The media was then removed and replaced with fresh media. E-PEBBLEs from Example 5 (50 μL to 100 μL of stock solution) were added to the wells and the cells incubated for 40 minutes. The cover slip was rinsed with Hank's Balanced Salt Solution (HBSS) (Invitrogen, Carlsbad, Calif.) containing 10 mmol N-2-Hydroxyethylpiperazine-N'-2-Ethane Sulfonic Acid (HEPES) and placed in a stainless steel cell chamber with 1 mL HBSS containing 10 mmol HEPES. In some cases, tetramethylrhodamine methyl ester (TMRM) (Molecular Probes, Eugene, Oreg.) dissolved in dimethyl sulfoxide (DMSO) was added to the chamber for a total concentration of ~50 nM to confirm mitochondrial fluorescence.

The entire chamber was mounted on a confocal microscope at room temperature (Olympus IX70 connected to a Life Science Resources UltraView equipped with an Ar—Kr laser and a Lambda 10-2 Sutter wheel from Sutter Instrument Co. Novato, Calif.) and examined with a 60× objective connected to a Z series motor. Four Z stacks were taken 1 minute apart, starting with time zero. At 3 minutes, 40 seconds, 1 μL of a carbonyl cyanide 3-chlorophenylhydrazone (CCCP) solution dissolved DMSO (concentration 12.2 mM) was added to the cell chamber (final CCCP concentration in chamber was 12.2 μM). A Z series of images (1 μm in thickness to allow for future three-dimensional reconstruction) was taken in the vertical plane every minute for 15 minutes and then every 5 minutes thereafter until the 30 minute time point. Slices analyzed were ~3-4 microns into the cell as measured from the bottom of the cell.

Cells were illuminated at 488 nm and the fluorescent images were collected at 600 nm (50 nm band pass), 700 nm (50 nm band pass), and 525 nm (50 nm band pass). A fourth channel for TMRM had a 568 nm excitation and an emission of 600 nm (50 nm band pass). Cells loaded with E-PEBBLEs only, E-PEBBLE matrix without dye (blank), free dye in water (at the same final concentration delivered in the E-PEBBLEs), TMRM only, or cells with nothing added to them provided the panel of controls used in the validation of the E-PEBBLEs. In some cases, C6 gliomas were used to further confirm the controls. In addition, cells exposed to E-PEBBLEs were treated with a HBSS/DMSO solution that contained no CCCP. In some cases, the final polymer coating was not applied and the loaded E-PEBBLEs added directly to the cells.

Repeated depolarizations of mitochondrial membrane potentials were performed as follows. Astrocytes were prepared as described above. Z series of Images were taken every minute for 15 minutes and every 5 minutes thereafter for 30 minutes. At time 3 minutes 50 sec, 1 μL of a CCCP solution (3.1 mM dissolved in DMSO and HBSS with HEPES; concentration in chamber was 3.1 μM) was added to the chamber. Starting at the 30 minute time point, images were again taken every minute until the 45 minute time point and every five minutes thereafter until the 60 minute time point. At time 33 minutes 50 seconds, a second dose of CCCP (3.1 mM) was added. The final concentration in the cell chamber for CCCP was 6.1 μM.

Cellular image analysis was performed as follows. Images of specific focal planes were transferred to the MetaMorph image analysis package and regions of interest (ROI) chosen consistent with TMRM-induced mitochondrial fluorescence, or the autofluorescent mitochondria of the astrocytes. In some cases, the images were expanded and regions of interest were also chosen from the surrounding cytosol. The average pixel intensity was determined for each ROI, and the emission ratio of the 525:700 nm images was then calculated. In some cases, the emission ratio of 600:700 nm was calculated. A reference emission ratio was obtained from an area that did not contain a cell, but had fluorescent intensity (e.g., residual E-PEBBLEs located on the coverslip). This reference point was used as the zero E field, and was the value used to calculate ΔR/R. The constructed calibration curve was then utilized to determine E fields. For the TMRM channel, the average pixel intensity was recorded.

Figure 15:
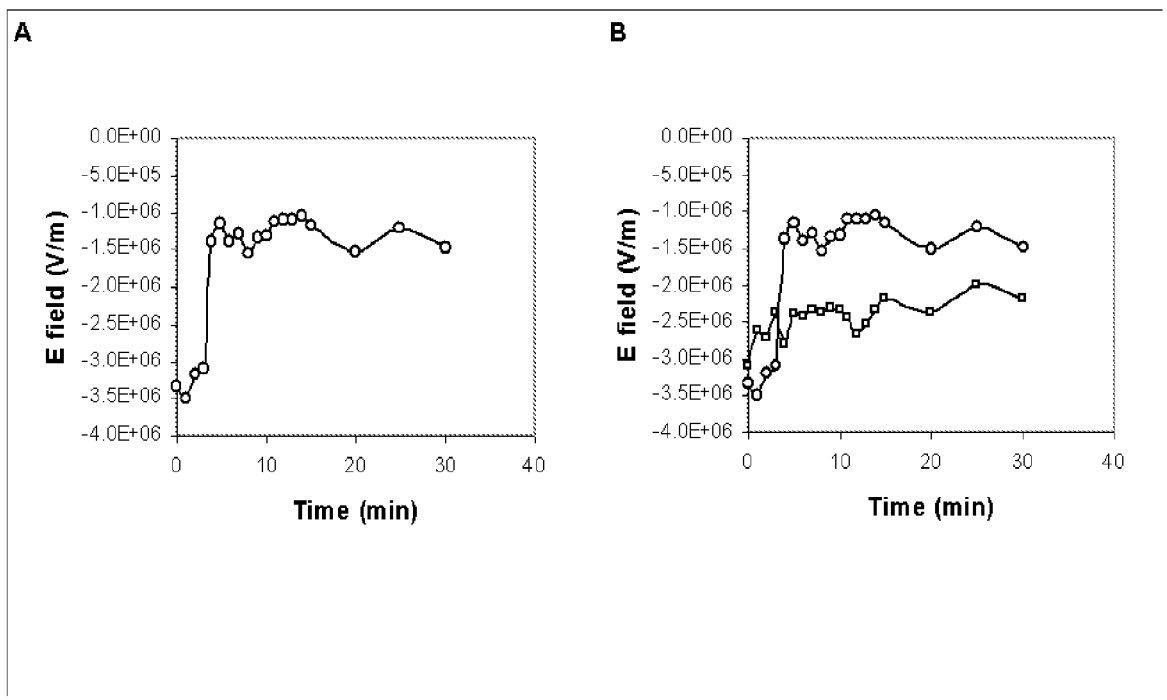
FIG. 15 panel A graphically depicts the E field of the membrane rapidly decreasing after the addition of CCCP at time 3 minutes and 40 seconds, and panel B compares the change in E field for a mitochondrial membrane using E-PEBBLEs, where either CCCP (circles) or DMSO (squares) is added to the cells at 3 minutes and 40 seconds.

Results of the mitochondrial membrane E field measurements are as follows. DITNC astrocytes, a model cell line with well-characterized respiratory profiles, were able to take up and tolerate the nanoparticles without further modification. Cells were challenged with the uncoupler CCCP, a chemical that causes rapid dissipation of the E field associated with the mitochondrial membrane. Regions of interest (ROI) were determined by locating areas of bright, punctuated fluorescence correlating spatially with mitochondrial fluorescence. The E-PEBBLEs emission ratio was then determined at the measurement time points. A reference emission ratio was obtained from an area that did not contain a cell, but had fluorescent intensity (residual E-PEBBLEs located on the coverslip). This reference point was used as the zero E field, and was the value used to calculate ΔR/R. Once the measurements were converted to ΔR/R, the values extracted from the external calibration curve were used to determine the E field at the region of interest. FIG. 15 A shows the E field of a mitochondrial region over time.

In FIG. 15 A, at times 0 minutes to 3 minutes, before the addition of CCCP, the mitochondrion should be fully polarized, with a large E field. The measured E field value is −3.3×$10^6$ V/m, which is lower than the value for a normal, polarized mitochondrion (−3×$10^7$ V/m). The E field is fairly stable, as measured by the E-PEBBLEs. After the addition of CCCP, the E field rapidly decreases. There then follows a slight repolarization of the mitochondrial membrane. This experiment demonstrates the ability of the localized E-PEBBLEs to follow fluctuations in the E field produced by a cellular component, in this case the E field associated with the mitochondrial membrane.

FIG. 6 B shows the comparison between cells exposed to CCCP and cells exposed to a control dose of DMSO. Focus is placed on the data points of minutes 3 and 4, the time points taken immediately before and after the addition of CCCP (or the corresponding control of DMSO) at time 3 min 40 s. For the cells exposed to CCCP, the E field at t=4 min is −1.4×$10^6$ V/m, a drop in E field of 55% from the data taken at minute 3 (−3.1×$10^6$ V/m), immediately preceding the addition of the CCCP. In four repeated experiments, the decrease between time points 3 min and 4 min has been as high as 90% and has never been lower than the 55% presented. The overall drop in E field from t=0 min to t=30 min is also 55%. In comparison, there is no drop in E field between time points 3 and 4 for the controlled data of DMSO. There is a slight increase in E field (14%), a result much different from the rapid decrease in E field in the data set containing the CCCP. The control data set has an overall decrease in E field (from t=0 min to t=30 min) of 29%.

In addition to the abrupt change in E field, which can be observed in FIG. 15 A, there is also an abrupt change in fluorescent intensity (decrease) in the cells when the CCCP is added. Neither the abrupt change in E field nor the decrease in fluorescent intensity is observed when the control dose of DMSO is added to the cells. There is neither an abrupt change in E field or fluorescent intensity in four repeated trials comparing the effects of CCCP versus the control dose of DMSO (note: in some cases, the repeated trials contained an additional tracking dye or all of the liquid volumes in the chamber were doubled).

Results of monitoring multiple E field fluctuations with the temperature-sensitive ratio. Astrocytes were incubated with E-PEBBLEs, transferred to a confocal microscope, and the mitochondrial membrane E field reduced with a small dose of CCCP. The mitochondria were then allowed to repolarize briefly, and a second dose of CCCP was applied. FIG. 16 shows the E field as a function of time for a mitochondrial region monitored by E-PEBBLEs using the 600:700 nm temperature-sensitive ratio (note: calibration curve used for determining E fields was constructed using the 600:700 nm emission ratio). After the application of the CCCP, the E field rapidly decreases, followed by a modest repolarization. The cells are then exposed to a second dose of CCCP. Again, there is a rapid decrease in the E field, followed by a repolarization. Following the E field using the 525:700 nm temperature-insensitive ratio produced similar trends (data not shown). The E-PEBBLEs followed the multiple changes in the mitochondrial E field for all applications of CCCP in all repeated trials (including trials using different concentrations of CCCP). These results demonstrate the E-PEBBLEs ability to monitor multiple E field fluctuations, even when using a temperature-sensitive emission ratio.

Figure 17:
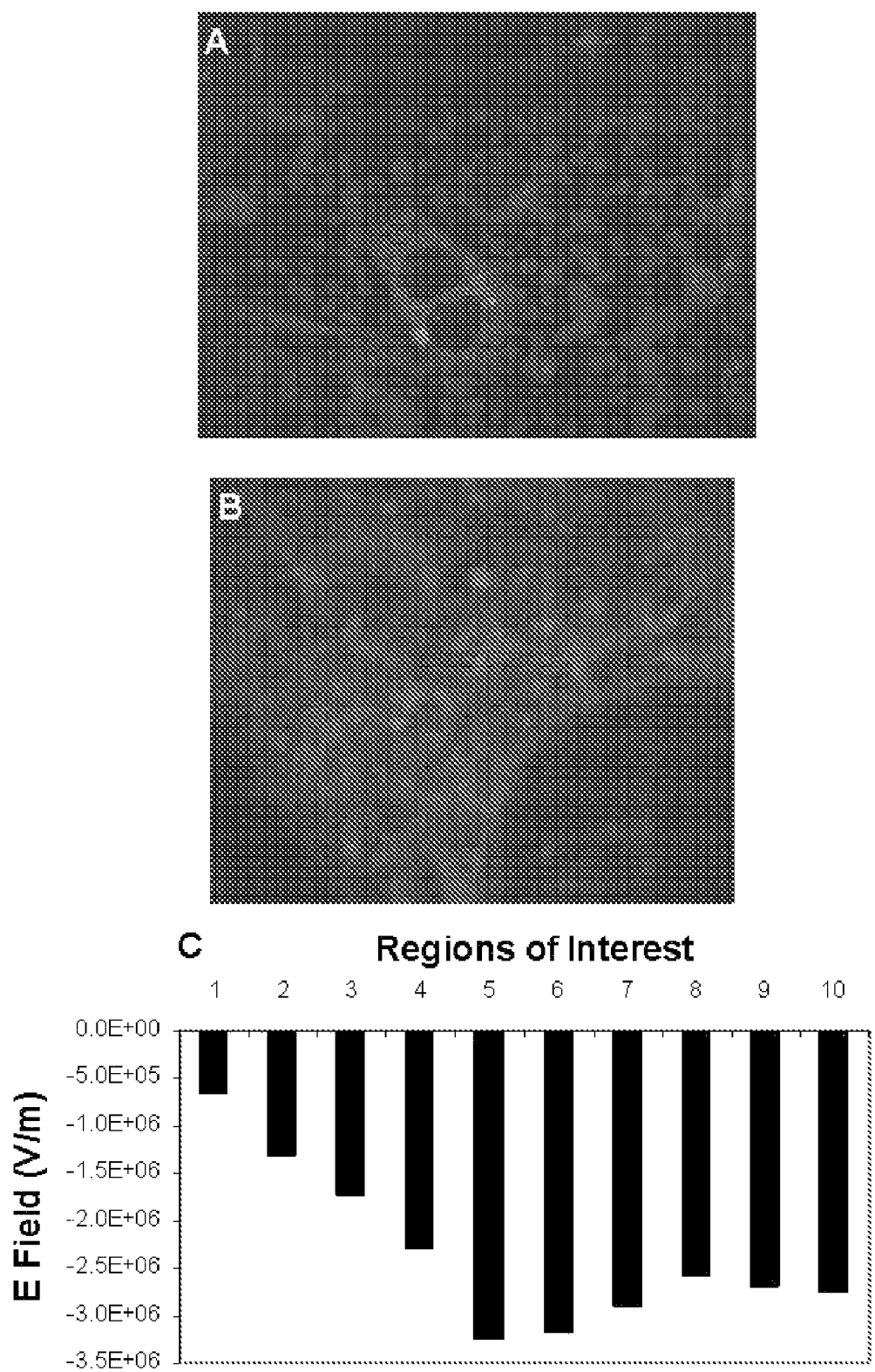
FIG. 17 panel A is a fluorescence photomicrograph of astrocytes incubated with E-PEBBLEs, where the middle cell contains the region analyzed (blue line, 4.5 microns); panel B shows an enlarged image of the cellular region analyzed (both membrane and cytosolic regions), where the regions are numbered 1-10 from left to right and region 5 contains a mitochondrion (brightly fluorescent region), while regions 6-10 cross over other mitochondrial regions, with the total length of the regions of interest being 4.5 microns; and panel C graphically depicts the E field for the regions of interest before the addition of CCCP, with the highest E field seen in region 5.

Results of the cytosol E field measurements are as follows. FIG. 17 A shows astrocytes incubated with E-PEBBLEs. The nanoparticles are taken up by the cells, and localize throughout the cell, but are excluded from the nucleus. Mitochondria appear as bright punctuated regions, whereas E-PEBBLEs have diffuse fluorescence (FIG. 17 B). An enlarged region of the middle cell in the image (FIG. 17 B) shows ROI containing both mitochondrial regions (regions 5-10) and cytosolic regions (regions 14). The E field for all of these ROI was determined using the external calibration curve (FIG. 17 C). The E field associated with the mitochondrial membrane drops significantly and rapidly with distance from the polarized mitochondrial membrane (region 5). However, the spatial picture is complicated by the presence of mitochondria above and below the plane of analysis. As the ROI crosses other mitochondrial regions (regions 6-10), the E field again increases. Although the E field intensity never again achieves the maximal intensity measured for the in-plane mitochondrion, the E field is still measurable several microns away from the mitochondria. The E-PEBBLEs have measured E fields extending away from the mitochondria and into the cytosol in over five separate trials.

The nanoparticles may be used to track changes in E fields associated with organelles, in this case, mitochondria. Referring again to FIG. 15, the E field associated with a mitochondrion before and after the addition of CCCP is shown. Before the addition of CCCP, the E field is about $-3.3 \times 10^6$ V/m, which is almost an order of magnitude lower than a fully polarized inner mitochondrial membrane. This result may be explained by the fact that the E-PEBBLEs are not actually inside the inner mitochondrial membrane. The E-PEBBLEs themselves may be adjacent to the mitochondrial outer membrane or simply close to the mitochondria. Repeating the above experiment several times, as well as analyzing different mitochondrial regions in the same cell, produces varying E fields (although the depolarization trend after the addition of CCCP is similar for all of the experiments). The E-PEBBLEs, in contrast to a naked voltage dye, can be at varying distances from the mitochondria. Thus, the resulting lower E field values could be due to the E field diminishing as it passes through the cell to the E-PEBBLEs. In addition, the mitochondria themselves may be in different respiratory states, and hence different E field states.

The E-PEBBLEs localize throughout the cell but are excluded from the nucleus, as indicated by the diffuse fluorescence present in the cells after coincubation with the E-PEBBLEs (FIG. 17 A, punctuated brightness is from autofluorescent mitochondria). Due to their relatively small size, the exact location of individual particles cannot be determined with the confocal microscope setup. Colocalization studies indicate that some, but not all, of the particles are in the lysosomes of the cell (data not shown). EM studies to determine nanoparticle distribution proved inconclusive, as the membrane is slightly damaged during nanoparticle entry (as indicated by PI staining), causing cells to rupture during fixation. Although the cellular membrane is damaged by nanoparticle entry, there are viable cells present, even after 48 h of constant incubation with the nanoparticles as determined by assay and examination with a fluorescent microscope (data not shown). Cell groups that appeared visually robust (i.e., elongate with little or no ruffling or blebbing of the membrane) were used for analysis.

After the CCCP is added to the cells, there is a rapid decrease in the E field that is not observed when only DMSO is added to the cells. As the dose of CCCP is relatively small (total concentration in the chamber is 12.2 mM), the E field associated with the mitochondrial membrane does not go to zero. In addition, the E field does not remain at the lower E field value but can increase over time, indicating a repolarization of the mitochondrial membrane.

A control dose of only DMSO does not produce the dramatic decrease in mitochondrial E field as seen with the corresponding application of CCCP. There is a slight decrease in E field over the entire time course of the experiment. The decrease of the E field may be partly due to photobleaching of the dye or the cells themselves becoming stressed as a result of the experimental conditions (over half an hour on an unheated stage in physiological buffer). In addition, since the nanoparticles do slightly damage the cells as indicated by PI staining, this damage may be showing up as a decrease in the mitochondrial E field.

Cells exposed to free dye in an aqueous solution did not fluoresce, providing compelling evidence that the dye must be incorporated into the nanoparticles to be taken up by the cells. Controls of E-PEBBLEs with no dye incorporated into the particles, or cells with nothing added to them, did not show a response to changing E-fields.

The E-PEBBLEs not only track E field changes rapidly but can also track multiple E field fluctuations. As a mitochondrion is repeatedly challenged with small doses of CCCP (a quarter of the concentration used in the preceding experiment), the E-PEBBLEs register first the drop in the E field and, subsequently, the repolarization of the E field (FIG. 16). The repolarization is possibly due to the small doses of CCCP or a subsequent "wash-out" effect. The same happens even when a temperature-sensitive emission ratio is used. This result demonstrates the E-PEBBLEs' ability to track multiple changes in the E field during a time course experiment. In addition, the particles may be selectively targeted to different regions of the cell, simply based on the exterior coating of the particles (data not shown).

From the above results it becomes clear that, in contrast to the traditional methods, the E-PEBBLEs may be used throughout the entire cell volume instead of being confined to the membrane regions. Thus, the above results demonstrate the ability of the nanoparticles to measure E fields outside of the lipid bilayers, whereas all voltage dye and patch-clamp techniques are constrained to measurements inside the membranes. If microelectrodes were used to measure nonmembranebound potentials, they would have first to puncture the external membrane. In addition, the electrodes do not have the ability to measure multiple regions simultaneously (and also require reference electrodes). Thus the E-PEBBLEs significantly increase the kind and amount of E field information obtainable from cells.

The data shown in FIG. 17 demonstrate the potential of the E-PEBBLEs to provide cellular-wide E field maps containing electrical information that originates from both membrane and nonmembrane regions in either individual or multiple optical slices arising from confocal imaging that can be reconstructed for a three-dimensional E field profile. The E field increases sharply as the ROI in the cytosol region approach the mitochondrion in region 5. The E field then slightly dissipates as the ROI extend back into the cytosol. The E-PEBBLE technique is sensitive enough that the E fields arising from mitochondria in a lower focal plane are also observed (regions 6-10). The E-PEBBLEs coupled with confocal microscopy thus provide a method to construct a complete electrical profile of a living cell, spanning both membrane and nonmembrane regions. Analyzing regions far away from mitochondrial regions still produces an E field value, supporting the picture of an electrically complex environment inside the cell.

EXAMPLE 7

Calibration of a Nanoparticle Thermometer

Figure 18:
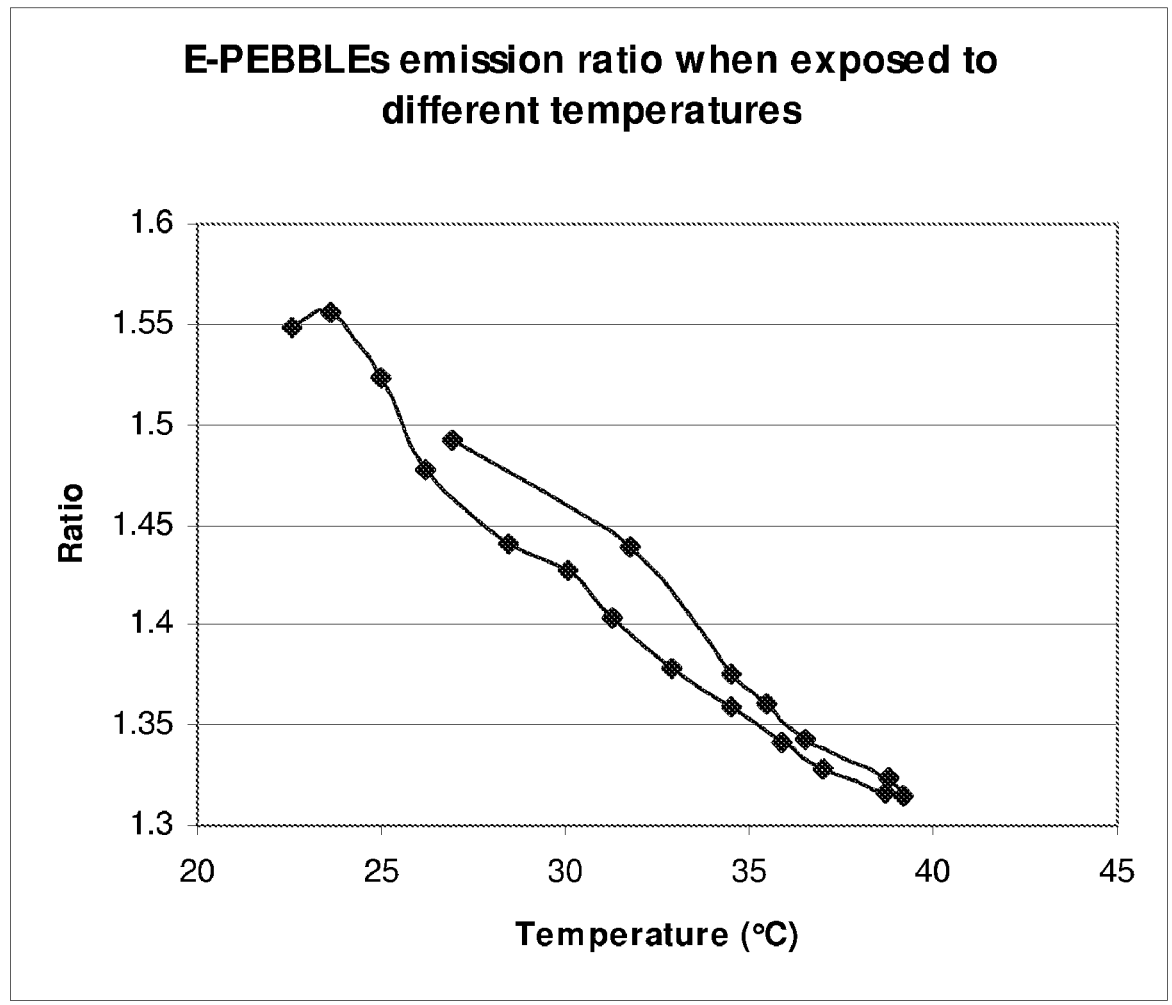
FIG. 18 graphically depicts the fluorescence emission spectra ratio for E-PEBBLEs through a heating and cooling cycle.

A solution of E-PEBBLEs (150 μL stock in 3 mL), similar to those synthesized in Example 5, was placed in a pre-heated chamber containing a glass cover slip bottom. Temperature measurements and corresponding emission spectra were taken approximately every minute as the solution heated to over 37° C. The chamber was then allowed to cool, and the temperature and emission spectra were again taken until the solution reached room temperature. Emission spectra were taken on an Olympus IMT-II (Lake Success, N.Y., USA) inverted fluorescence microscope with an Acton Research Corp. spectrograph and a Hamamatsu HC230 CCD interfaced with an Intel Pentium computer. The CCD was controlled by the software program LABVIEW (National Instruments, Austin, Tex.). Excitation was from a Xenon lamp, and the microscope was fitted with standard Olympus blue filter cube. Emission ratios were calculated for 600 nm/700 nm by taking the average intensity from 575 nm to 626 nm over 675 nm to 726 nm. Emission ratios were then plotted versus temperature to obtain the calibration curve shown in FIG. 18.

EXAMPLE 8

Methods of Using E-PEBBLEs to Measure and Compare Cellular E-Fields in Mitochondrial and Microfilament Regions SY5Y cells (neurons) are used in this example. E-PEBBLEs, similar to those synthesized in Example 5, are taken up by the cells as indicated by Z series analysis. The neurons appeared to tolerate the E-PEBBLEs better than C6 and DITNC1 cells, as visual inspection indicated more viable cells remaining on the cover slip after treatment with the nanoparticles.

Figure 19:
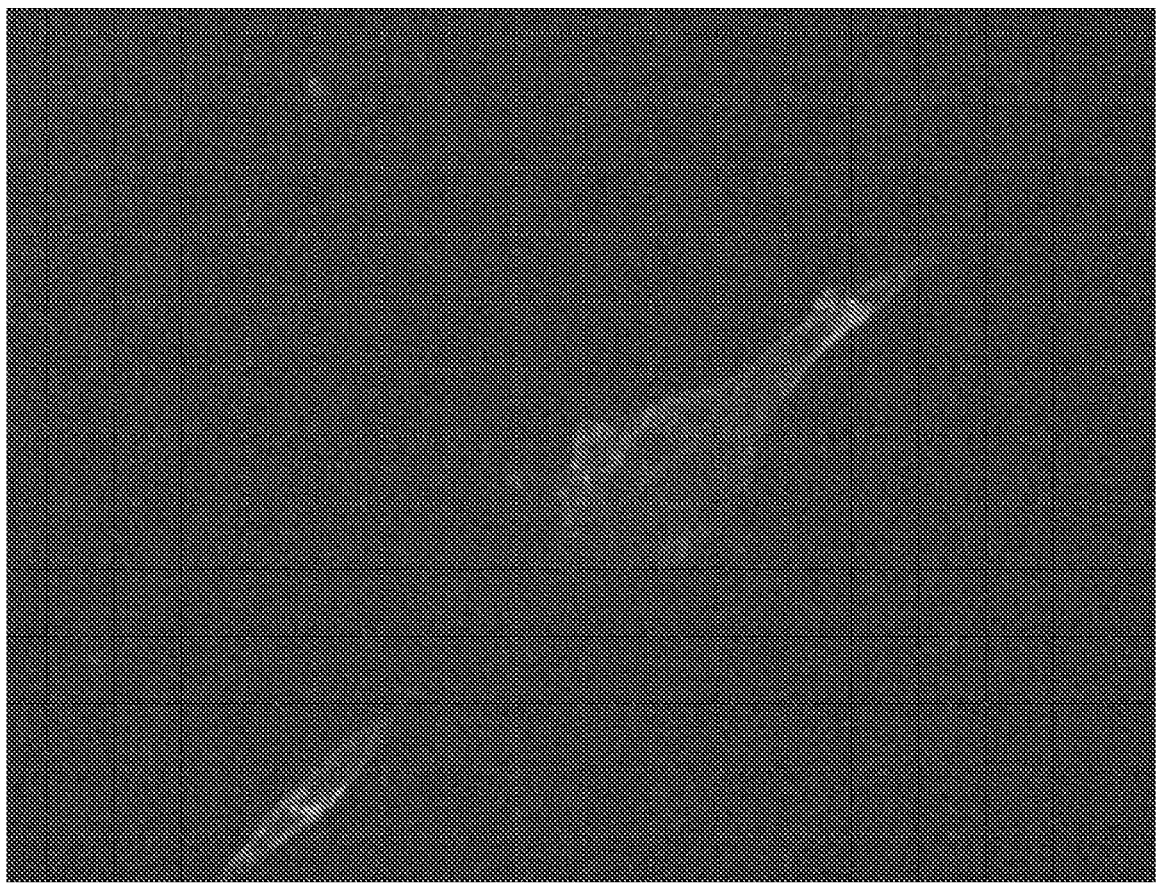
FIG. 19 is a fluorescence photomicrograph of neurons co-incubated with E-PEBBLEs before addition of KCl.
Figure 20:
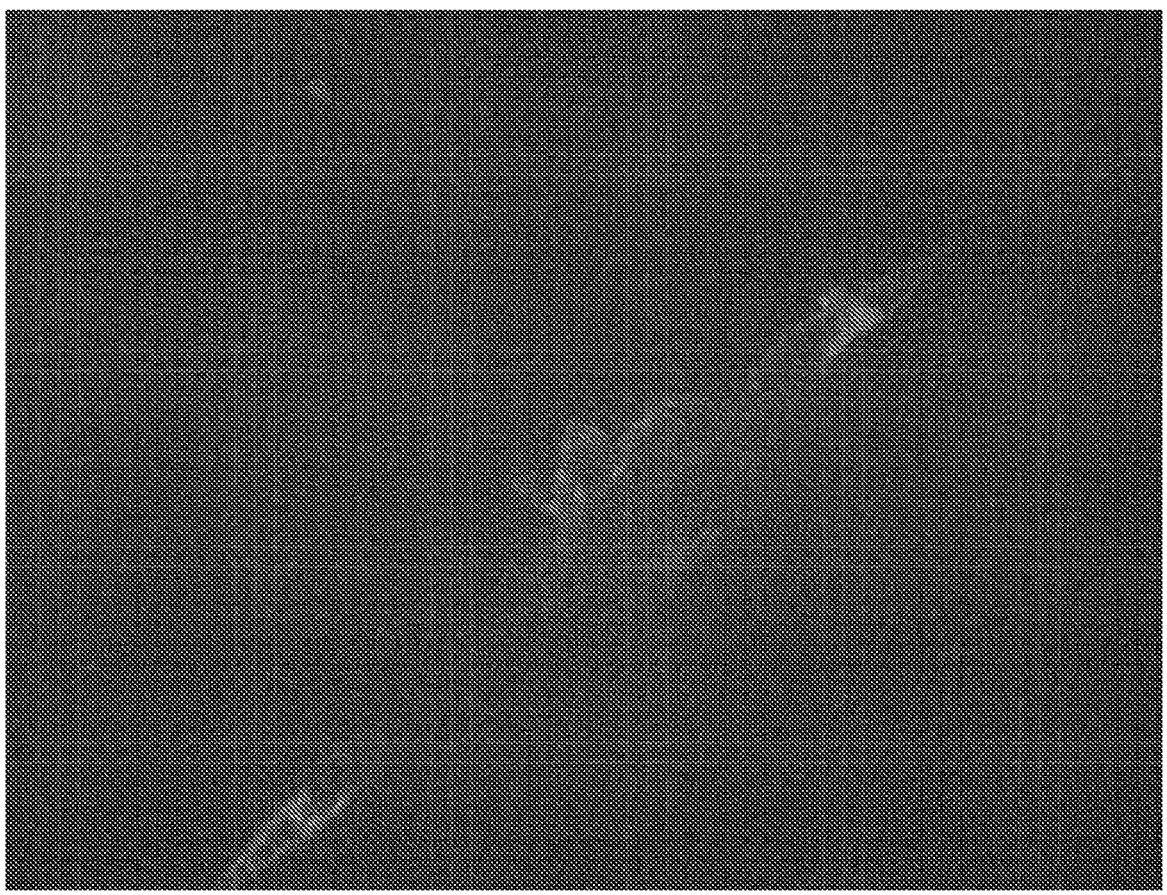
FIG. 20 is a fluorescence photomicrograph of neurons co-incubated with E-PEBBLEs after addition of KCl.

Neurons were co-incubated with E-PEBBLEs and then rinsed with HBSS to remove any exterior nanoparticles. The cells were then allowed to recover in the incubator for 30 min. Once the cell chamber was taken to the UltraView, a second dose of E-PEBBLEs was added so that the nanoparticles would be both inside and outside of the cells (for possible tracking of the action potential on all sides of the membrane). The effects of the action potential were visible, but as the image is a little grainy, it is unclear whether the actual firing was caught on tape. FIG. 19 is an image of the neurons before KCl addition and FIG. 20 is an image of the neurons after KCl addition.

There is a decrease in the E-PEBBLE fluorescent intensity, indicating a depolarization. There is also a broadening of the fluorescent intensity surrounding the exterior membrane of the cells. It is difficult to see the broadening with the still images, but it can be seen using a recorded movie of the cells.

Figure 21:
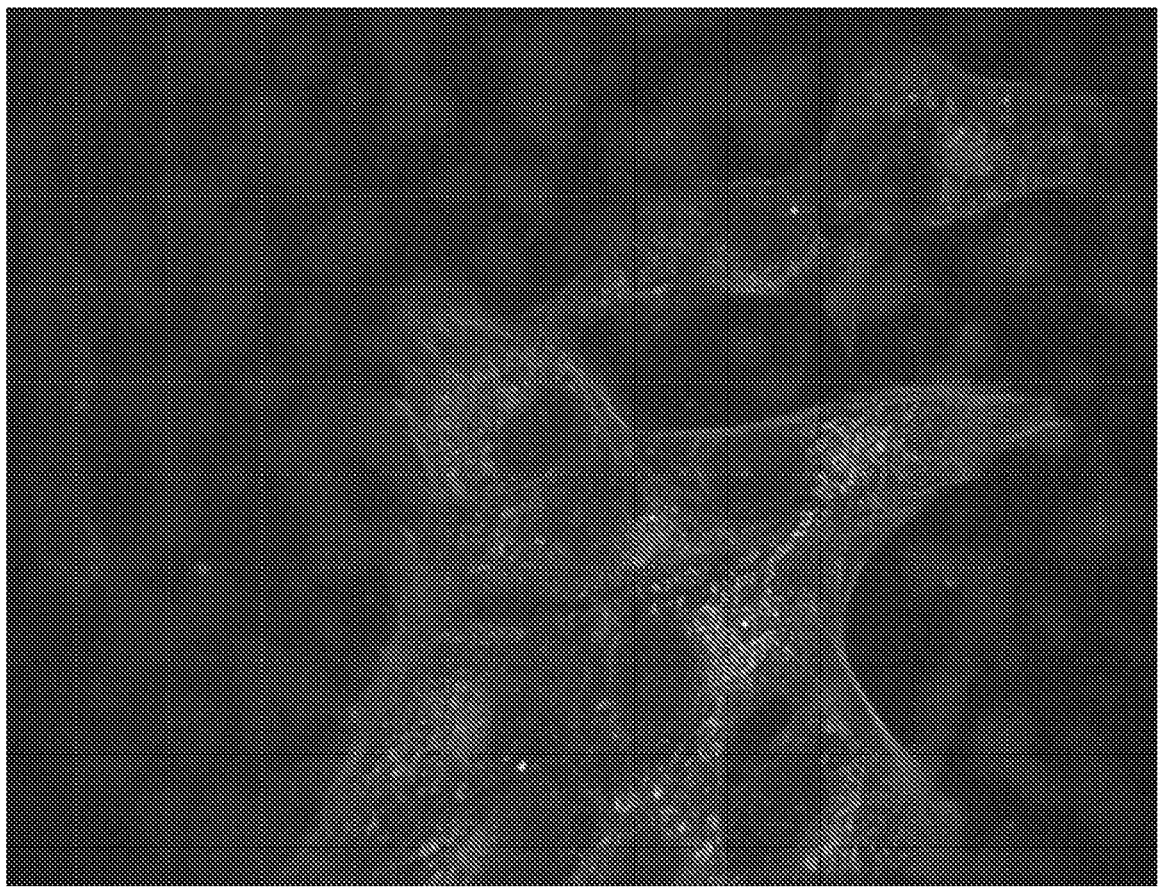
FIG. 21 is a fluorescence photomicrograph of astrocytes co-incubated with E-PEBBLEs and alexafluor-phalloidin with an emission filter to show the E-PEBBLEs and the mitochondria.
Figure 22:
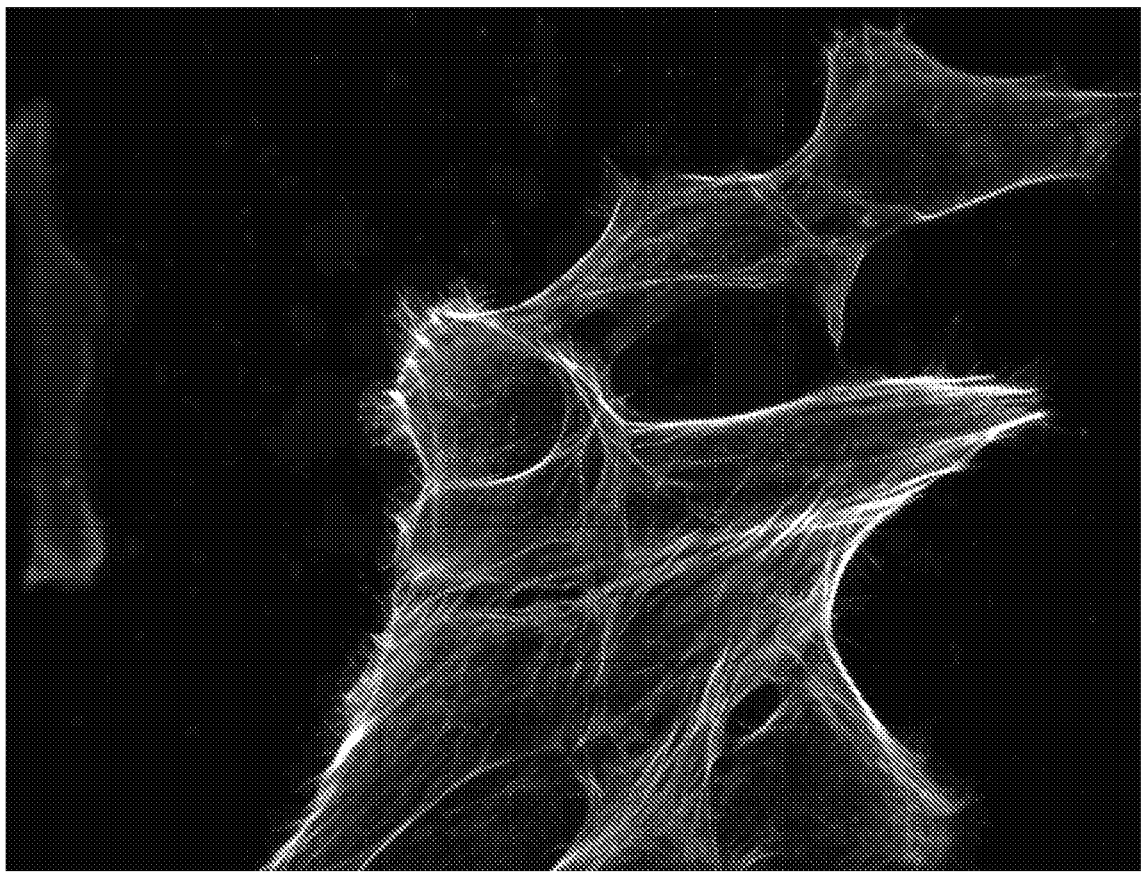
FIG. 22 is a fluorescence photomicrograph of astrocytes co-incubated with E-PEBBLEs and alexafluor-phalloidin with an emission filter to show the microfilaments.

Microfilaments in astrocytes. Astrocytes were co-incubated with E-PEBBLEs and alexafluor-phalloidin (a microfilament stain). The fluorescence arising from the mitochondria, E-PEBBLEs, and microfilaments were able to be resolved though use of different fluorescent emission filters. Mitochondria and E-PEBBLEs are shown in FIG. 21 and microfilaments are shown in FIG. 22.

Figure 23:
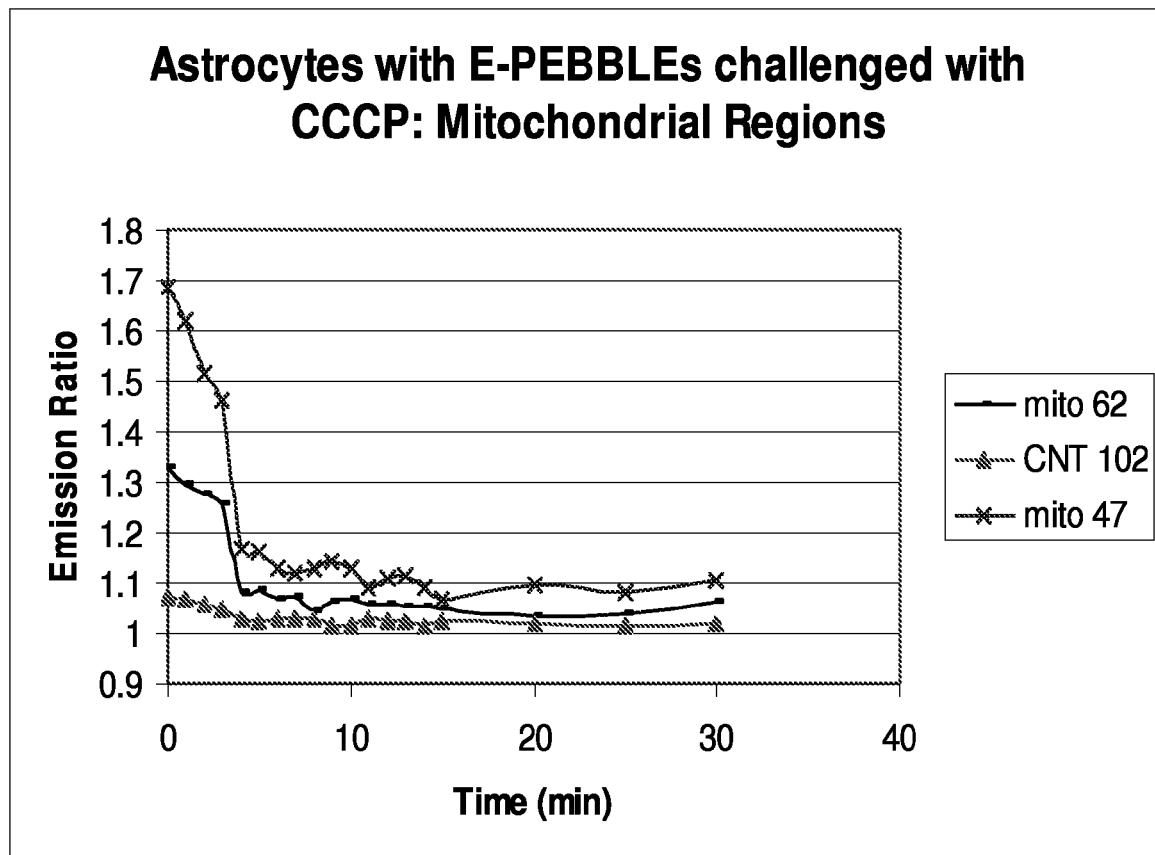
FIG. 23 graphically depicts the emission ratio for mitochondrial regions following CCCP challenge.

The cells were challenged with CCCP at 3 min 45 sec using normal experimental parameters, as described in Example 7. The mitochondrial regions show the normal depolarization (CNT is a control region outside of the cell), as shown in FIG. 23.

Figure 24:
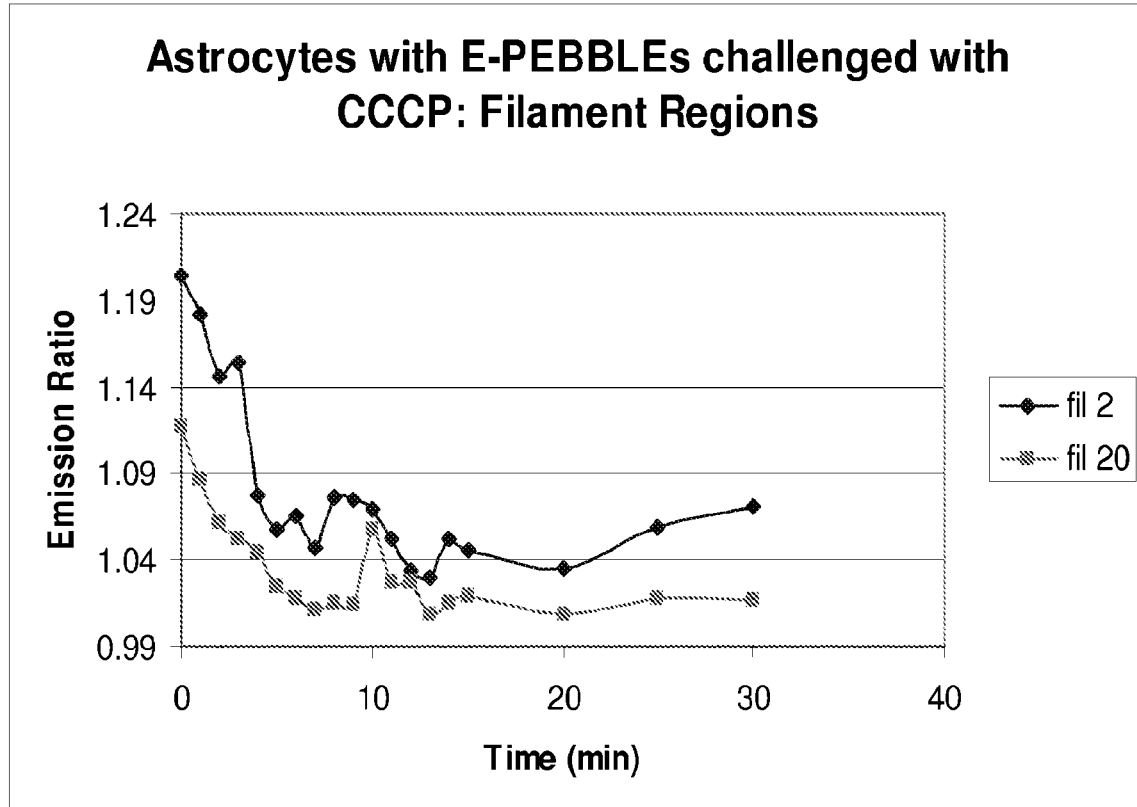
FIG. 24 graphically depicts the emission ratio for microfilament regions following CCCP challenge.

Microfilament regions show a different response. In particular, there is a spike at the 10-15 minute time point, which was seen in several filaments in two separate experiments, as shown in FIG. 24.

Figure 25:
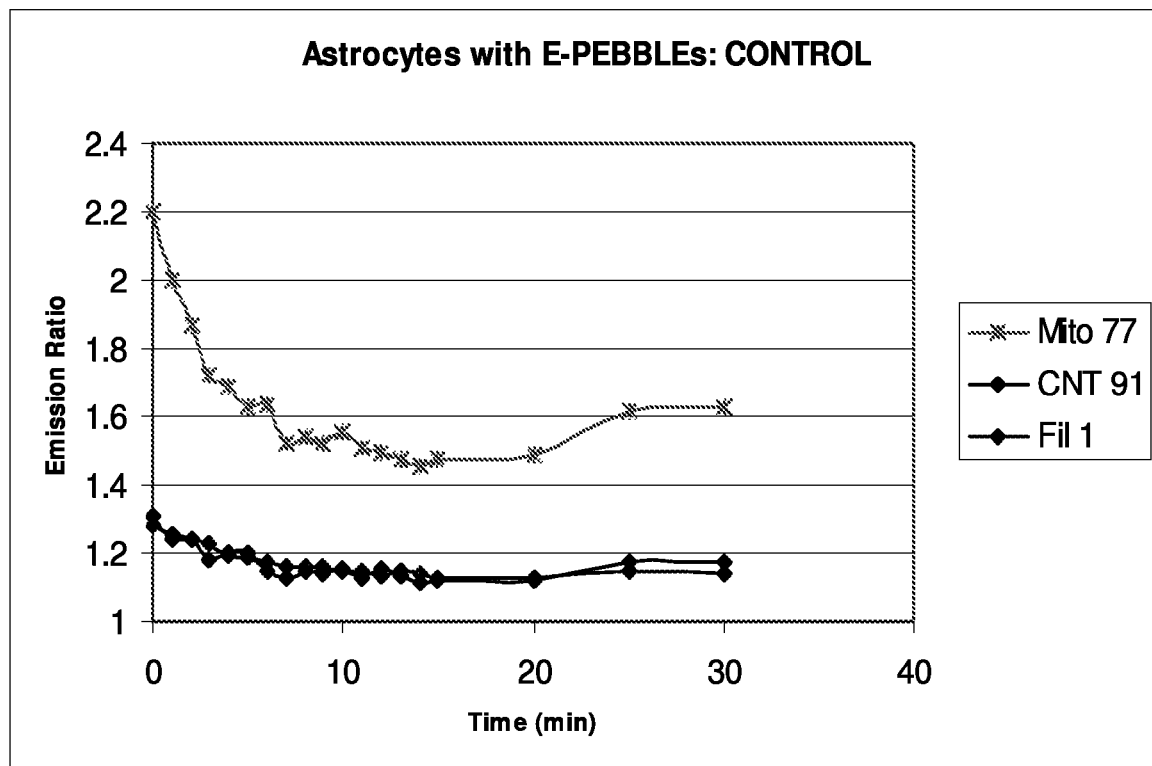
FIG. 25 graphically depicts the photobleaching of the mitochondrial and microfilament regions.

FIG. 25 demonstrates that the microfilament stain photobleaches faster than the E-PEBBLEs, as shown by the filament emission channel. As a result, much of the decrease shown in the filament graph could be due to bleaching. In addition, the control of adding only HBSS to the cells (no CCCP) showed a photobleaching effect for all regions of the cell.

There is a difference in the E fields between the mitochondrial and filament regions when the cell is challenged, but what is actually observed with the filaments can be investigated using additional experiments, for example, in order to determine the correlation between the mitochondria, toxin, and microfilament response.

The examples and other embodiments described herein are exemplary and not intended to be limiting in describing the full scope of compositions and methods of this technology. Equivalent changes, modifications and variations of specific embodiments, materials, compositions and methods may be made within the scope of the present technology, with substantially similar results.

What is claimed is:

1. A nano-optical voltmeter particle comprising:
   an organic core having at least one voltage-sensitive dye;
   at least one polymeric shell substantially surrounding said organic core; and
   a positively-charged coating material.

2. The nano-optical voltmeter particle of claim 1, wherein the polymeric shell comprises polymerized silane.

3. The nano-optical voltmeter particle of claim 1, wherein the polymeric shell comprises polymerized silane reacted with a silane capping group.

4. The nano-optical voltmeter particle of claim 1, wherein the voltage-sensitive dye comprises di-4-ANEPPS.

5. The nano-optical voltmeter particle of claim 1, wherein the voltage-sensitive dye changes at least one of fluorescence, luminescence, and absorbance in response to a change in electric field.

6. The nano-optical voltmeter particle of claim 1, further comprising a silane capping layer comprising monoethoxy silane.

7. The nano-optical voltmeter particle of claim 1, wherein the particle is about 1 nm to about 100 nm in diameter.

8. A nano-optical voltmeter particle comprising:
an organic core having at least one voltage-sensitive dye;
at least one polymeric shell substantially surrounding said organic core, wherein the polymeric shell is formed from polymerized silane headgroups of a mixed micelle comprising a long-chain organosilane and a surfactant; and
a second silane layer comprising an amine.

9. The nano-optical voltmeter particle of claim 8, further comprising a targeting molecule coupled to the amine of the second silane layer.

10. The nano-optical voltmeter particle of claim 8, further comprising an exterior coating of poly(diallyldimethylammonium chloride).

* * * * *